United States Patent [19]
Honda et al.

[11] Patent Number: 6,053,906
[45] Date of Patent: Apr. 25, 2000

[54] ULTRASONIC OPERATION APPARATUS

[75] Inventors: Yoshitaka Honda, Tokorozawa; Tomohisa Sakurai, Sagamihara, both of Japan

[73] Assignee: Olympus Optical Co., Ltd., Tokyo, Japan

[21] Appl. No.: 09/102,999

[22] Filed: Jun. 22, 1998

[30] Foreign Application Priority Data

| Jun. 25, 1997 | [JP] | Japan | 9-168924 |
| Jan. 21, 1998 | [JP] | Japan | 10-009678 |
| Jun. 16, 1998 | [JP] | Japan | 10-168651 |
| Jun. 16, 1998 | [JP] | Japan | 10-168652 |

[51] Int. Cl.$^7$ ................................................. A61B 17/70
[52] U.S. Cl. ............................................ 606/1; 606/169
[58] Field of Search ................... 604/22; 601/2; 600/439; 606/1, 169–171

[56] References Cited

U.S. PATENT DOCUMENTS

| 4,223,676 | 9/1980 | Wuchinich | 604/22 |
| 4,614,178 | 9/1986 | Harlt et al. | 601/2 |
| 4,750,488 | 6/1988 | Wuchinich et al. | 604/22 |
| 4,791,915 | 12/1988 | Barsotti et al. | 604/2 |
| 4,979,952 | 12/1990 | Kubota et al. | 606/169 |
| 4,989,588 | 2/1991 | Kubota et al. | 604/22 |
| 5,076,276 | 12/1991 | Sakurai et al. | 604/22 |
| 5,151,085 | 9/1992 | Sakarai et al. | 604/22 |
| 5,160,317 | 11/1992 | Costin | 604/22 |
| 5,447,509 | 9/1995 | Mills et al. | 606/1 |
| 5,449,370 | 9/1995 | Vaitekunas | 606/169 |
| 5,520,633 | 5/1996 | Costin | 604/22 |
| 5,728,130 | 3/1998 | Ishikawa et al. | 606/185 |

*Primary Examiner*—Francis J. Jaworski
*Attorney, Agent, or Firm*—Frishauf, Holtz, Goodman, Langer & Chick, P.C.

[57] ABSTRACT

A control unit comprises a load state detector for detecting a load state of a load acting on a treatment section when the treatment section is put in contact with a living tissue, and a bar-graph display for indicating the load state in relation to ultrasonic oscillation on the basis of a detection result from the load state detector.

27 Claims, 15 Drawing Sheets

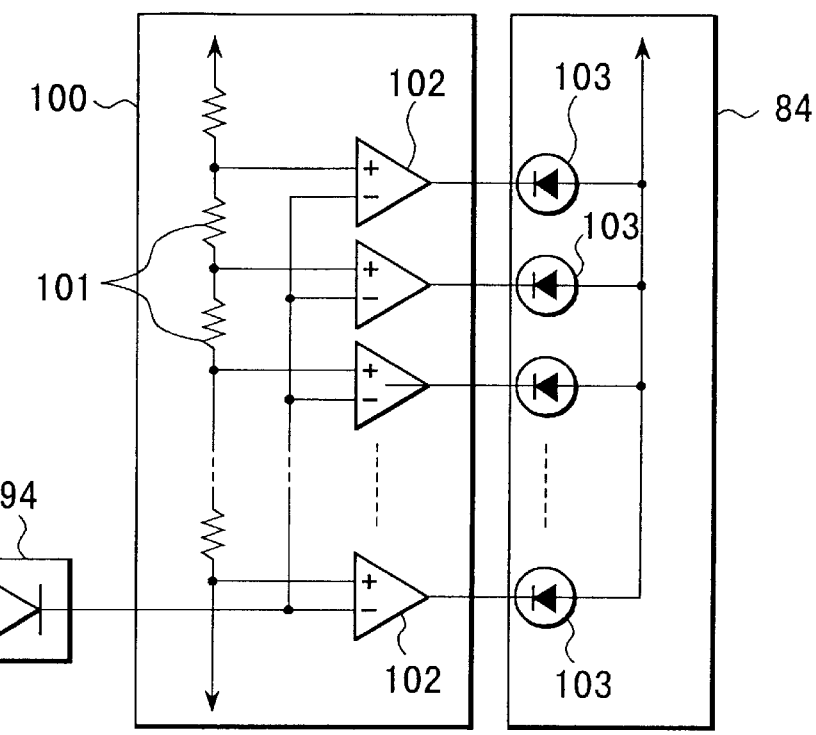
F I G. 16
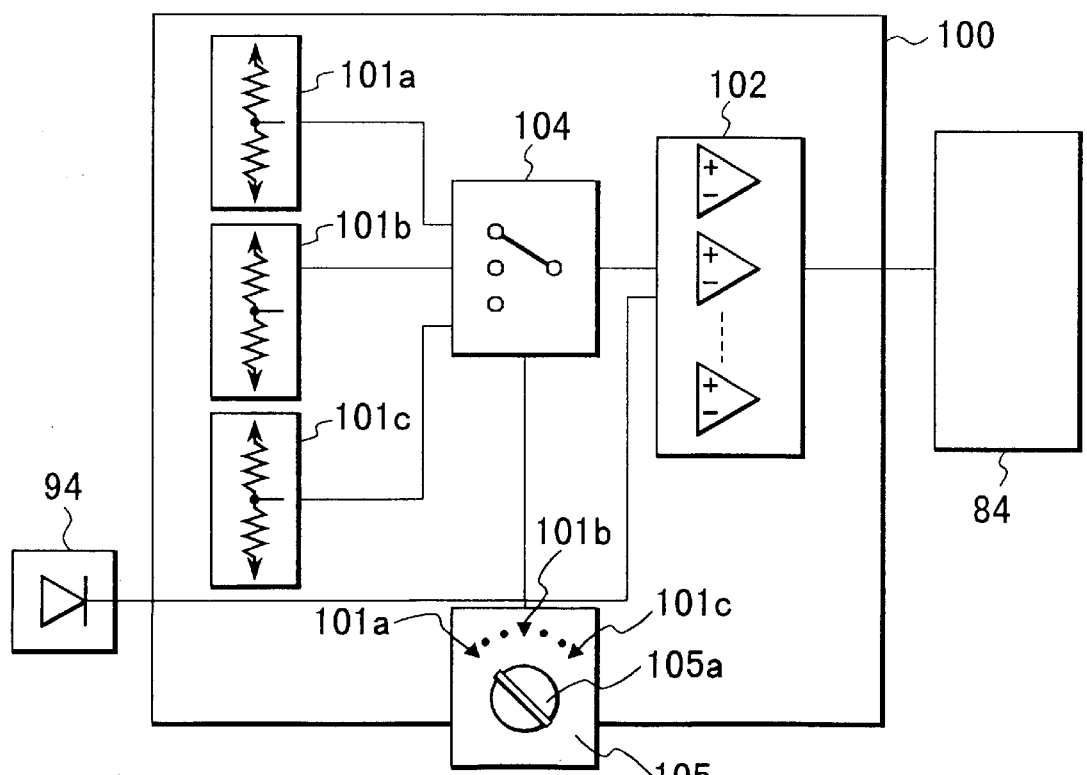
F I G. 17

ULTRASONIC OPERATION APPARATUS

BACKGROUND OF THE INVENTION

The present invention relates to an ultrasonic operation apparatus for treating a living tissue by ultrasonic oscillation.

Various operation apparatuses using ultrasonic waves, such as devices for ultrasonic coagulation/cutting, ultrasonic clip welders or ultrasonic trocars, are conventionally known as applied techniques of ultrasonic oscillation. In this type of ultrasonic operation apparatus, a handpiece having a treatment unit for treating a living tissue contains an ultrasonic oscillator for producing ultrasonic oscillation and a probe for transmitting ultrasonic oscillation from the ultrasonic oscillator to the treatment unit.

When the ultrasonic operation apparatus is used, ultrasonic oscillation is transmitted from the ultrasonic oscillator to the treatment unit via the probe in a state in which the treatment unit is put in contact with a region to be treated, and the living tissue is treated by the ultrasonic oscillation.

When the trocar or coagulation operation apparatus is used, the user holds the handpiece and puts the treatment unit of the handpiece in contact with the living tissue. At this time, the pressure force for pressing the treatment unit on the living tissue becomes a load on the ultrasonic oscillator. If the user applies an excessive force while using the ultrasonic operation apparatus, the force for pressing the living tissue increases. In this case, the load on the ultrasonic oscillator increases excessively so that the oscillator cannot oscillate. Consequently, the ultrasonic operation apparatus cannot perform a normal ultrasonic treatment function.

BRIEF SUMMARY OF THE INVENTION

The present invention has been made in consideration of the above problem, and its object is to provide an ultrasonic operation apparatus capable of properly utilizing respective treatment functions by means of ultrasonic oscillation and limiting excessive energy supply to the living tissue.

In order to achieve the object, there is provided an ultrasonic operation apparatus having:
  a handpiece with a treatment section for treating a living tissue;
  an ultrasonic oscillator built in the handpiece;
  a probe for transmitting ultrasonic oscillation from the ultrasonic oscillator to the treatment section; and
  a drive circuit unit connected to the handpiece and including a drive circuit for driving the ultrasonic oscillator,
    wherein the drive circuit unit comprises:
      load state detection means for detecting a load state of a load acting on the treatment section when the treatment section is put in contact with the living tissue; and
      load state indicating means for indicating the load state in relation to the ultrasonic oscillation on the basis of a detection result from the load state detection means.

In this invention, at the time of ultrasonic treatment, a variation in magnitude of a voltage applied to the ultrasonic oscillator is displayed on the load state indicating means, and the load state relative to ultrasonic oscillation is indicated. The load state indicating means indicates the load state, for example, as a variation in light amount of a lamp, a pitch of sound, or a volume of sound. Thus, the operator is informed of the load state.

According to this invention, there is also provided an ultrasonic operation apparatus having:
  a handpiece with a treatment section for treating a living tissue;
  an ultrasonic oscillator built in the handpiece;
  a probe for transmitting ultrasonic oscillation from the ultrasonic oscillator to the treatment section; and
  a drive circuit unit connected to the handpiece and including a drive circuit for driving the ultrasonic oscillator,
    wherein the drive circuit unit comprises:
      load state detection means for detecting a load state of a load acting on the treatment section when the treatment section is put in contact with the living tissue,
      the load state detection means includes a detachable connection portion permitting an electrical relay between the handpiece and the drive circuit unit, and signal detection means for detecting a signal supplied to the ultrasonic oscillator, and
      the signal detection means is detachably connected to external display means and includes an output section for outputting a control signal for displaying the load state relative to the ultrasonic oscillation on the external display means and indicating the load state on the basis of a detection result of the signal detection means when the external display means is connected.

According to this invention, at the time of ultrasonic treatment, a variation in a voltage applied to the ultrasonic oscillator is displayed on external display means, and the load state relative to ultrasonic oscillation is indicated.

According to this invention, there is also provided an ultrasonic operation apparatus having:
  a handpiece with a treatment section for treating a living tissue;
  an ultrasonic oscillator built in the handpiece;
  a probe for transmitting ultrasonic oscillation from the ultrasonic oscillator to the treatment section; and
  a drive circuit unit connected to the handpiece and including a drive circuit for driving the ultrasonic oscillator,
    wherein the drive circuit comprises:
      constant current control means for performing a control to let a predetermined constant current to the ultrasonic oscillator;
      means for taking out a signal indicating a magnitude of a voltage applied to the ultrasonic oscillator;
      means for setting a limit to the amount of energy supplied to the ultrasonic oscillator; and
      energy limit control means for switching, when the amount of energy supplied to the ultrasonic oscillator has reached the set value set by the energy amount limit setting means, a constant current control system by the constant current control means to an energy amount limit control drive system for limiting the amount of energy supplied to the ultrasonic oscillator, thus driving the ultrasonic oscillator.

In this invention, the ultrasonic oscillator is driven with a constant current and the amplitude is controlled at a constant value. During the control, an upper limit value of energy, which can be set, is determined. When the supplied power has reached the upper limit value, further supply of power to the ultrasonic oscillator is stopped. Specifically, the drive system is switched to the constant voltage drive, and the energy supply amount is limited. Thus, excessive energy supply to the living tissue is limited and the safety is enhanced.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 16 shows a detailed structure of a display circuit and a bar-graph display according to the fourth embodiment;

FIG. 17 shows a modification of the display circuit according to the fourth embodiment;

DETAILED DESCRIPTION OF THE INVENTION

Figure 1:
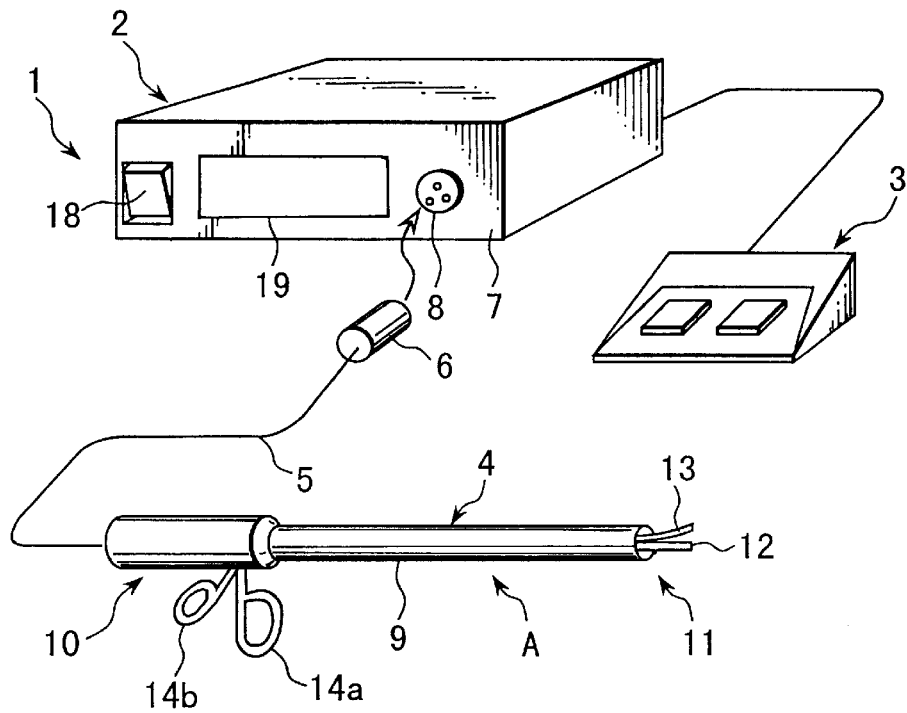
FIG. 1 shows a schematic structure of an entirety of an ultrasonic operation apparatus according to a first embodiment of the present invention.

A first embodiment of the present invention will now be described with reference to FIGS. 1 to 7B. FIG. 1 schematically shows the structure of an entirety of an ultrasonic operation apparatus 1 according to the embodiment. The ultrasonic operation apparatus 1 of this embodiment comprises a control unit 2, a footswitch 3 connected to the control unit 2, and a handpiece 4 of an ultrasonic treatment device.

A proximal end portion of a connection cable 5 is connected to the handpiece 4 of the ultrasonic treatment device. A distal end portion of the connection cable 5 is connected to a connector 6. A front panel 7 of control unit 2 is provided with an ultrasonic treatment device connector B. The connector 8 is detachably connected to the connector 6 of the ultrasonic treatment device.

Figure 2:
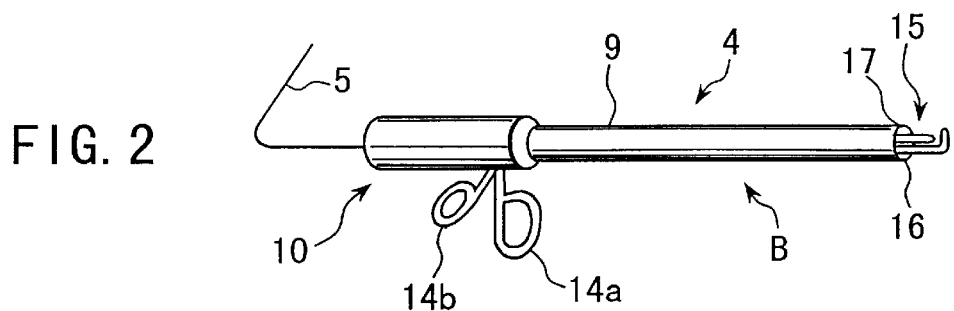
FIG. 2 is a perspective view showing an exchange treatment tool for the ultrasonic operation apparatus according to the first embodiment.

A first ultrasonic treatment device A shown in FIG. 1 or a second ultrasonic treatment device B shown in FIG. 2 may be used as the ultrasonic treatment device used in the ultrasonic operation apparatus 1 of this embodiment. The handpiece 4 of first ultrasonic treatment device A comprises an elongated sheath 9, a proximal-side operation section 10 coupled to a proximal end portion of the sheath 9, and a treatment section 11 provided at a distal end portion of the sheath 9.

The handpiece 4 contains an ultrasonic oscillator (not shown) for causing ultrasonic oscillation and a probe 12 for transmitting the ultrasonic oscillation from the ultrasonic oscillator to the treatment section 11. A holding portion 13 rotatably supported on the distal end portion of the sheath 9 is provided in the treatment section 11. The holding portion 13 can move toward and away from a distal end portion of the probe 12.

Figure 6:
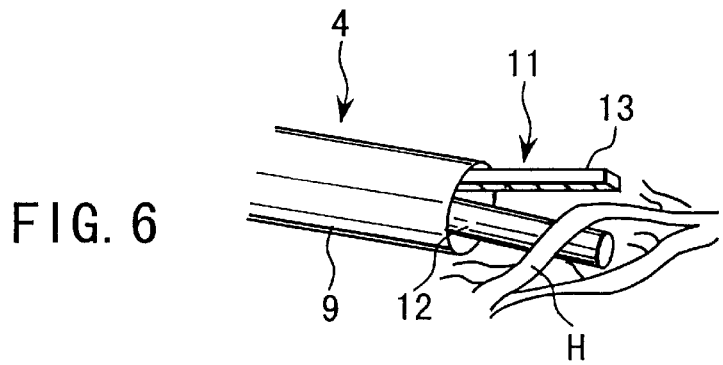
FIG. 6 is a perspective view showing a use state of a main part of the ultrasonic operation apparatus according to the first embodiment.

The operation section 10 on the proximal side of the handpiece 4 is provided with a fixed handle 14a and a movable handle 14b. The movable handle 14b is moved toward and away from the fixed handle 14a so that the holding portion 13 of treatment section 11 may be put in contact and out of contact with the distal end portion of the probe 12. In this case, when the movable handle 14b is moved toward the fixed handle 14a and closed, the holding portion 13 is rotated and closed toward the distal end portion of probe 12. Thus, as shown in FIG. 6, a living tissue H such as a blood vessel of the human body can be held between the holding portion 13 and the distal end portion of probe 12. In this state, if the ultrasonic oscillator in the handpiece 4 is driven, an ultrasonic treatment can be applied to the living tissue between the probe 12 and holding portion 13.

The handpiece 4 of second ultrasonic treatment device B is provided with a treatment section 15 having a structure different from the structure of the treatment section 11 of first ultrasonic treatment device A. The treatment section 15 comprises a substantially L-shaped receiving portion 16 fixed at the distal end portion of the sheath 9, and an abutment portion 17 axially slidably provided in the sheath 9. One of the receiving portion 16 and abutment portion 17 is coupled to the distal end portion of probe 12. When the movable handle 14b is moved toward and away from the fixed handle 14a of operation section 10, the abutment portion 17 of treatment section 15 can be put in contact and out of contact with the receiving portion 16. In this case, when the movable handle 14b is moved toward the fixed handle 14a and closed, the abutment portion 17 of treatment section 15 is slid toward the receiving portion 16 and the living tissue such as a blood vessel of the human body is held between the abutment portion 17 and receiving portion 16. In this state, if the ultrasonic oscillator in the handpiece 4 is driven, an ultrasonic treatment can be applied to the living tissue between the abutment portion 17 and receiving portion 16.

Figure 3:
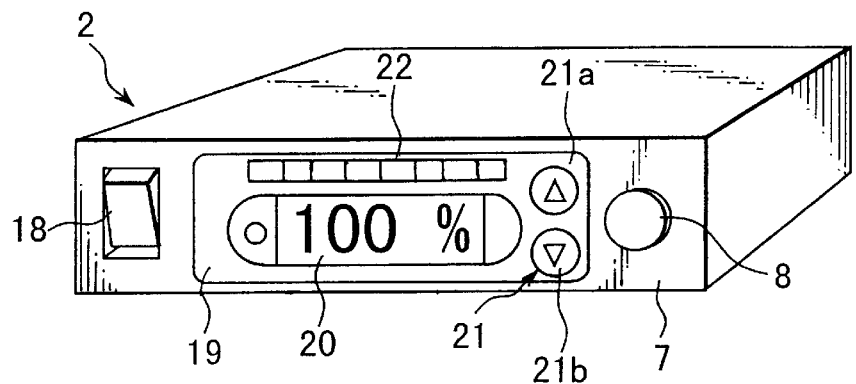
FIG. 3 is a perspective view showing a main body of the ultrasonic operation apparatus according to the first embodiment.

As is shown in FIG. 3, the front panel 7 of control unit 2 is provided with a power switch 18 and a display panel 19. The display panel 19 is provided with a setting display section 20 for indicating a set value of the magnitude (magnitude of amplitude) of the ultrasonic oscillator, a setting section 21, and a bar-graph display section (load state indicating means) 22 for indicating a load state on the ultrasonic oscillator. The setting section 21 includes a setting up-switch 21a and a setting down-switch 21b.

Figure 4:
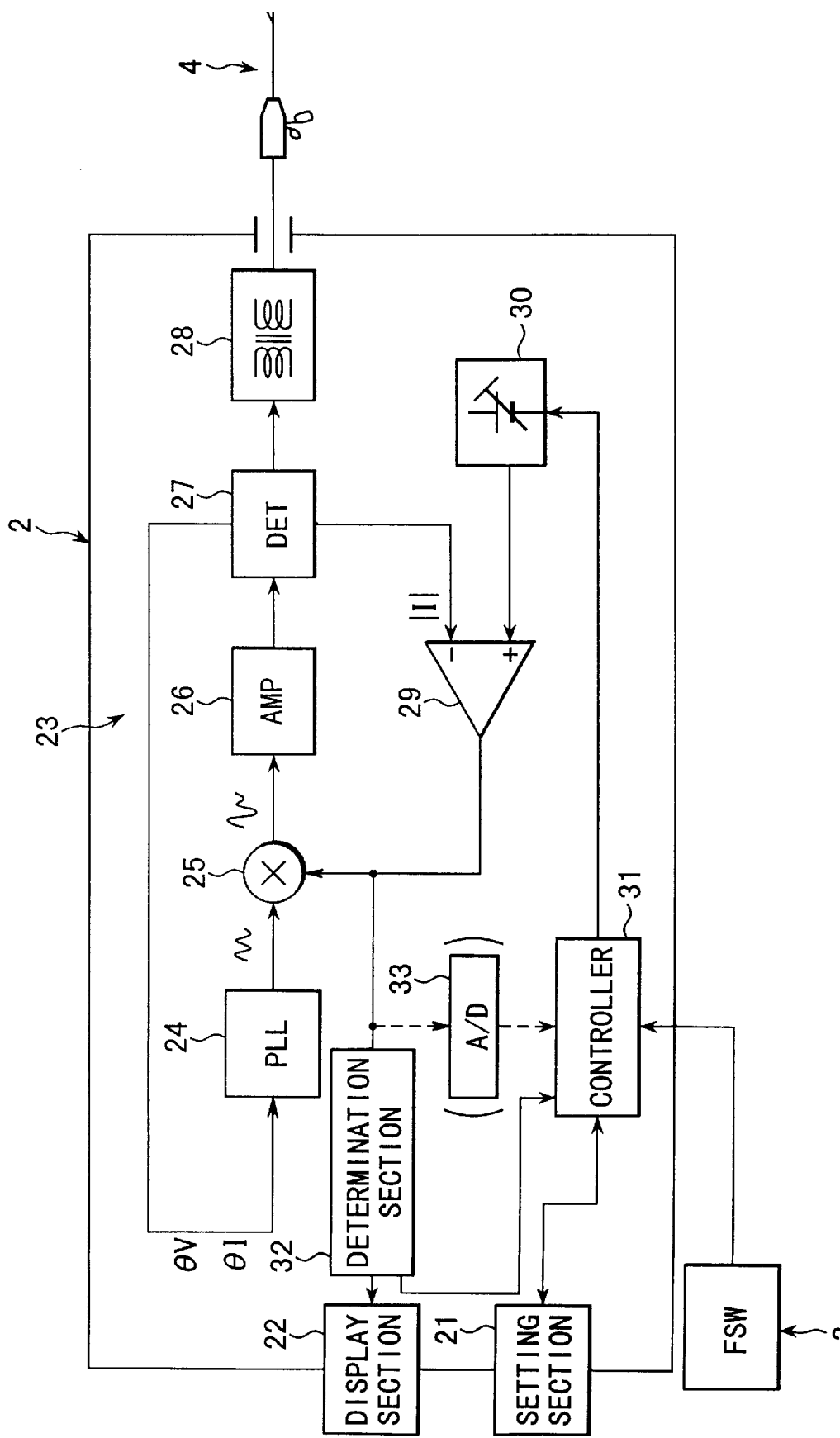
FIG. 4 shows a schematic structure of a drive circuit provided within the main body of the ultrasonic operation apparatus according to the first embodiment.

A drive circuit 23 having a structure shown in FIG. 4 is mounted within the control unit 2. The drive circuit 23 generates and amplifies an ultrasonic signal and supplies the signal to the ultrasonic oscillator in the handpiece 4. The drive circuit 23 includes an output circuit wherein a phase-locked loop (PLL) 24, a voltage control amplifier (VCA) 25 or a multiplier for constant-current driving, a power amplifier 26 for producing a current for supplying a power to the ultrasonic oscillator, a voltage/current detector 27, and an output transformer 28 are connected in series. An output port of the output transformer 28 is connected to the handpiece 4. The drive circuit 23 in the control unit 2 is separated from the handpiece 4 by the output transformer 28 with respect to DC.

The PLL 24 is a circuit for tracking a resonance frequency of the ultrasonic oscillator for resonance-point driving. The voltage/current detector 27 is connected to the PLL 24. The voltage/current detector 27 includes a circuit for detecting a phase signal of a voltage and a current for a PLL operation or detecting the magnitude of a current flowing in the ultrasonic oscillator.

The drive circuit 23 further includes a differential amplifier 29, a voltage generator 30, a controller 31, a determination section 32 and an A/D converter 33. The controller 31 is connected to the footswitch 3, the setting section 21 on the display panel 19, voltage generator 30, determination section 32 and an A/D converter 33.

One input terminal of the differential amplifier 29 is connected to the voltage/current detector 27, and the other input terminal is connected to the voltage generator 30. The voltage generator 30 generates a voltage proportional to an amplitude set through the setting section 21 on the display panel 19.

An output terminal of the differential amplifier 29 is connected to the voltage control amplifier 25. The differential amplifier 29 compares a set voltage produced from the voltage generator 30 on the basis of the set amplitude and the magnitude of a current value detected by the voltage/current detector 27. The differential amplifier 29 supplies an amplified output to the voltage control amplifier 25 so that the compared set voltage and the magnitude of the current value may be equalized. Thus, the magnitude of the voltage applied to the ultrasonic oscillator is controlled to obtain a constant current. This construction provides a constant current loop.

Figure 5:
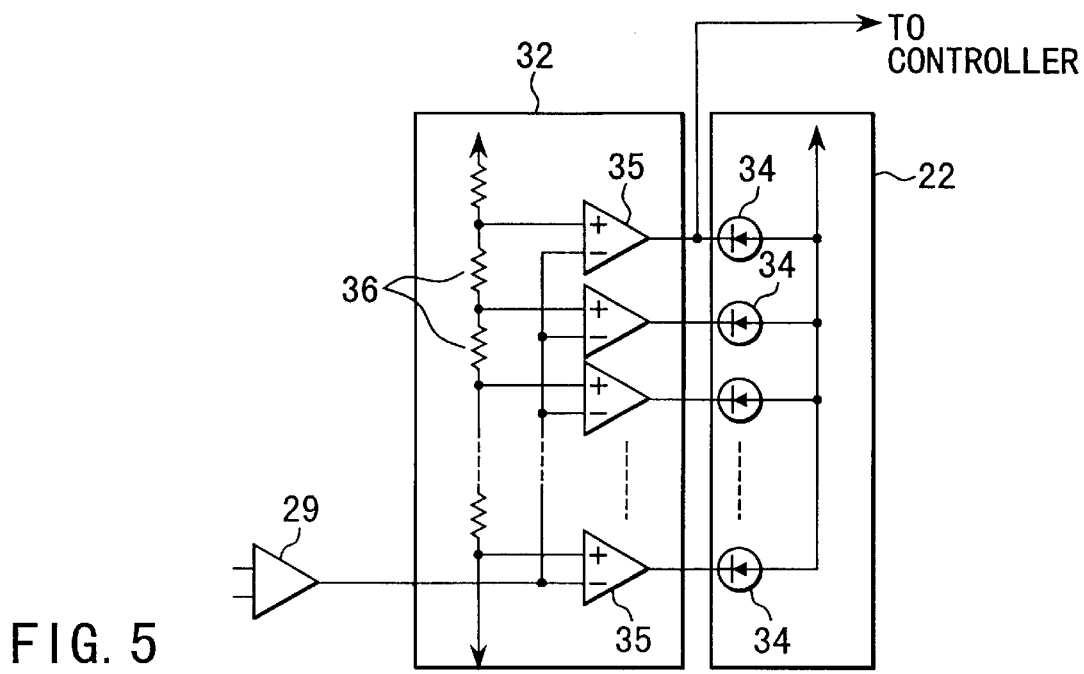
FIG. 5 shows a schematic structure of a main part of the driving circuit according to the first embodiment.

The output terminal of the differential amplifier 29 is connected to the determination section 32. The determination section 32 is connected to the bar-graph display section 22 of display panel 19. The bar-graph display section 22 includes a plurality of LEDs 4, as shown in FIG. 5. In addition, the determination section 32 includes comparators 35 connected individually to the LEDs 34 of bar-graph display section 22 and resistors 36.

An output signal from the differential amplifier 29 is input to the determination section 32. The determination section 32 generates data on a load which is displayed on the bar-graph display section 22. Since the magnitude of an output voltage from the output transformer 28 is proportional to an input to the multiplier of the voltage control amplifier 25, the input signal to the multiplier of voltage control amplifier 25 represents the magnitude of impedance. Accordingly, the determination section 32 displays the state of load variation on the bar-graph display section 22 in the form of, e.g. a bar graph, on the basis of the output from the differential amplifier 29, i.e. the input signal to the voltage control amplifier 25. At this time, the multi-stage comparators 35 of the determination section 32 receive the output signal from the differential amplifier 29, and individually control the on/off states of LEDs 34 of the bar-graph display section 22. The state of load variation in relation to ultrasonic oscillation is displayed in the form of a bar graph on the basis of the on/off states of LEDs 34 of bar-graph display section 22.

It is possible to adopt such a structure that the determination section 32 supplies to the controller 31 a signal obtained when a voltage value received by the multi-stage comparators 35 takes a maximum value, and the control circuit indicates the state of load variation relative to the ultrasonic oscillation.

It is also possible to adopt such a structure that the output signal from the differential amplifier 29 is received by the A/D converter 33 and converted to digital data, the digital data is input to the controller 31, and on the basis of the input data the controller 31 directly drives the LEDs 34 of bar-graph display section 22.

Figures 7A, 7B:
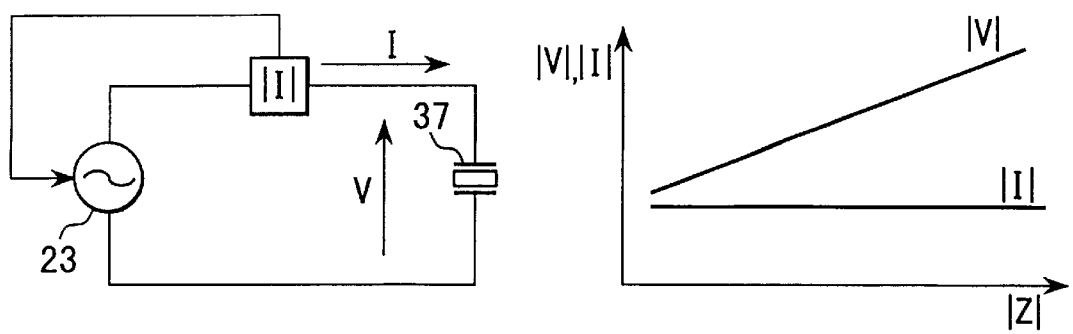
FIG. 7A shows a schematic structure of the drive circuit within the main body of the ultrasonic operation apparatus according to the first embodiment.
FIG. 7B is a characteristic graph showing a state in which a constant voltage drive control is performed by the drive circuit of the ultrasonic operation apparatus according to the first embodiment.

The operation of the above-described structure will now be described. FIG. 7A shows a simplified electric circuit of the entire ultrasonic operation apparatus according to the present embodiment. In FIG. 7A, reference numeral 37 denotes the ultrasonic oscillator in the handpiece 4. While the ultrasonic operation apparatus 1 of this embodiment is being used, the amplitude of ultrasonic oscillation of the ultrasonic oscillator 37 is proportional to a flowing current. |I|. Thus, if the value of this current is fed back to perform a constant-voltage drive by the drive circuit 23 in the controller 2, stable oscillation amplitude is obtained independently of a load variation.

FIG. 7B shows states of variations of voltage |V| and current |I| while a constant-current drive control is being performed by the drive circuit 23 of ultrasonic operation apparatus 1 shown in FIG. 7A. In FIG. 7B, the abscissa indicates the impedance |Z| and the ordinate the voltage |V| and current |I|.

Since the constant-current drive is performed, the current value is kept constant even if the load impedance |Z|, i.e. a mechanical load on the ultrasonic oscillator 37, varies. At this time, the voltage |V| increases in proportion to the impedance |Z|.

Since the amplitude of the ultrasonic oscillation is proportional to the current flowing in the ultrasonic oscillator 37, the constant-current control is performed in order to maintain the amplitude of ultrasonic oscillation from the ultrasonic oscillator 37 at the set value. At this time, in the case of the coagulation/cutting apparatus, as shown in FIG. 6, the ultrasonic oscillator 37 is driven to apply ultrasonic oscillation in the state in which the living tissue H such as a blood vessel of the human body is held between the holding portion 13 of handpiece 4 and the distal end portion of the probe 12.

During the operation, if the holding force for holding the living tissue H between the holding portion 13 of handpiece 4 and the distal end portion of the probe 12 is increased excessively, the impedance |Z| increases. As a result, the voltage |V| is saturated even if the constant current is to be supplied from the drive circuit 23 to the ultrasonic oscillator 37, and the set amplitude cannot be maintained. In an extreme case, the ultrasonic oscillation is stopped and the coagulation operation for the living tissue H cannot be effected. Thus, the amount of force for holding the living tissue H, such as a blood vessel of the human body, between the holding portion 13 of handpiece 4 and the distal end portion of probe 12 becomes one of the parameters which determine the degree or speed of treatment for the living tissue H. For example, in the case of an ultrasonic trocar used as an applied device of the handpiece 4, if a great force is applied to pierce the ultrasonic trocar into the paries, the force for pushing the trocar increases excessively. Consequently, the impedance |Z| increases excessively and the ultrasonic oscillation may stop.

To solve the above problem, in the ultrasonic operation apparatus 1 of this embodiment, the bar-graph display section 22 is provided on the display panel 19 of control unit 2, and the state of load (impedance |Z|) on the ultrasonic oscillation is indicated on the bar-graph display section 22 in the form of a bar graph on the basis of the on/off states of LEDs 34 of bar-graph display section 22. Thus, the user may view the bar graph on the bar-graph display section 22 of display panel 19 and easily confirm the state of load (impedance |Z|) on ultrasonic oscillation.

The apparatus with the above structure has the following advantages. Specifically, in this embodiment, when the ultrasonic operation apparatus 1 is used, the force applied by the operator to handle the handpiece 4 is displayed and indicated in the form of a bar graph on the bar-graph display section 22 on the display panel 19 of control unit 2. Thus, the operator can view the bar graph on the bar-graph display section 22 and easily confirm the force applied by the operator to handle the handpiece 4. Accordingly, the operator can easily control the force for closing the movable handle 14b of handpiece 4, and stably perform a coagulation operation for the living tissue H.

Figure 8:
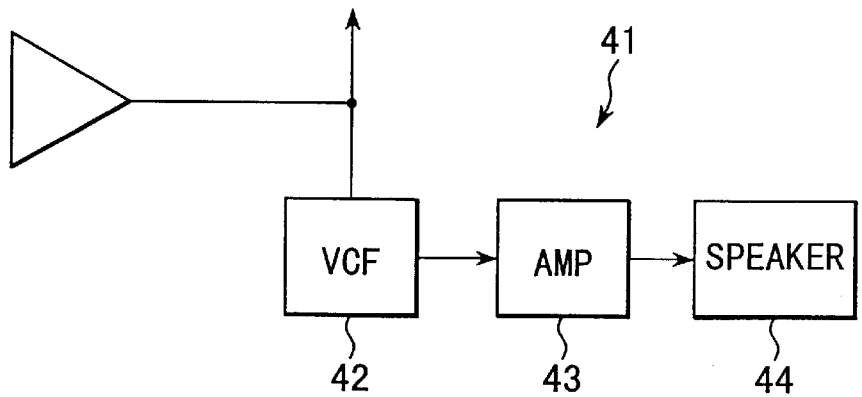
FIG. 8 shows a schematic structure of a main part of a drive circuit according to a modification of the first embodiment.

FIG. 8 shows a modification of the first embodiment (see FIGS. 1 to 7B). In this modification, while the ultrasonic operation apparatus 1 is being used, the variation in impedance |Z| is indicated not by the bar graph but by sound quality variation indicating means 41 which indicates the variation as a variation in sound quality. Specifically, the sound quality variation indicating means 41 of this modification comprises a VCF oscillator 42 connected to the output terminal of the differential amplifier 29, a speaker amplifier 43 and a speaker 44. The output from the differential amplifier 29 is received by the VCF oscillator 42 and a variation in voltage is converted to a variation in frequency. An output signal from the VCF oscillator 42 is received by the speaker amplifier 43 and the sound quality of the output of the speaker 44 is varied.

Instead of varying the sound quality by varying the output from the differential amplifier 29, it is possible to vary the cycle of continuous sound or the volume of sound. In addition, the bar graph in the first embodiment may be adopted in combination.

Figure 9:
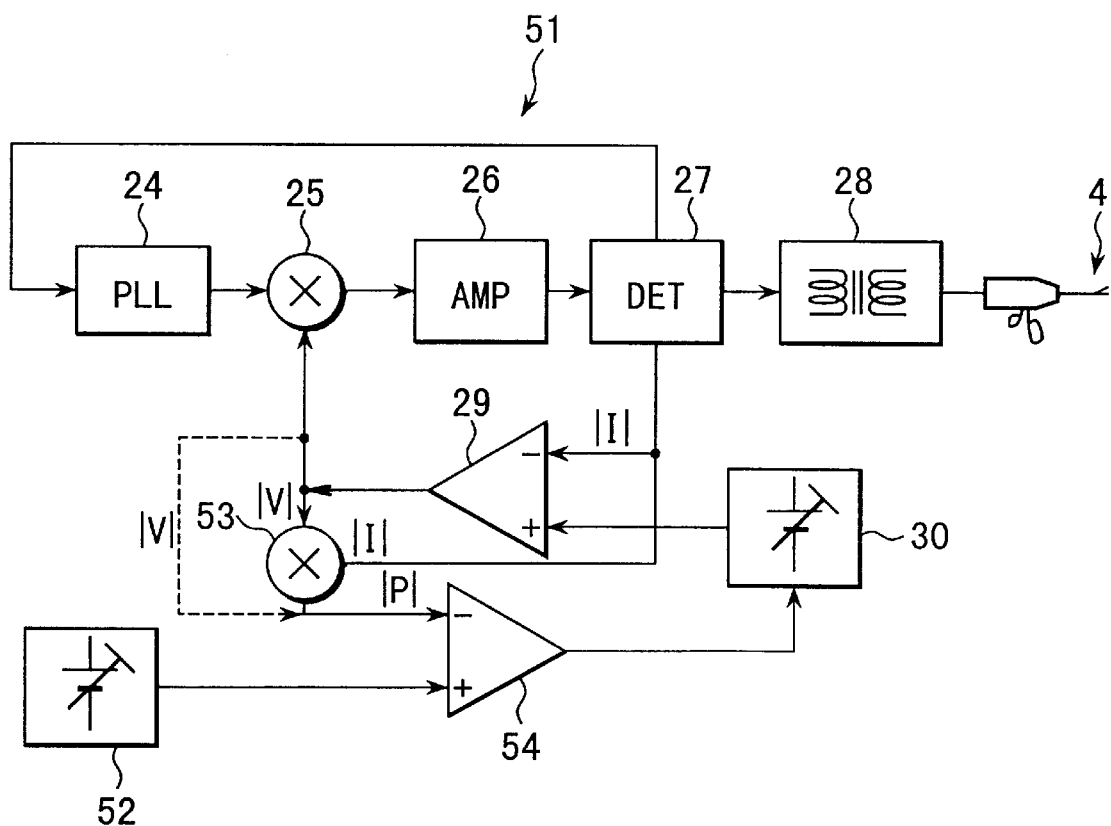
FIG. 9 shows a schematic structure of a drive circuit provided within a main body of an ultrasonic operation apparatus according to a second embodiment of the invention.
Figure 10:
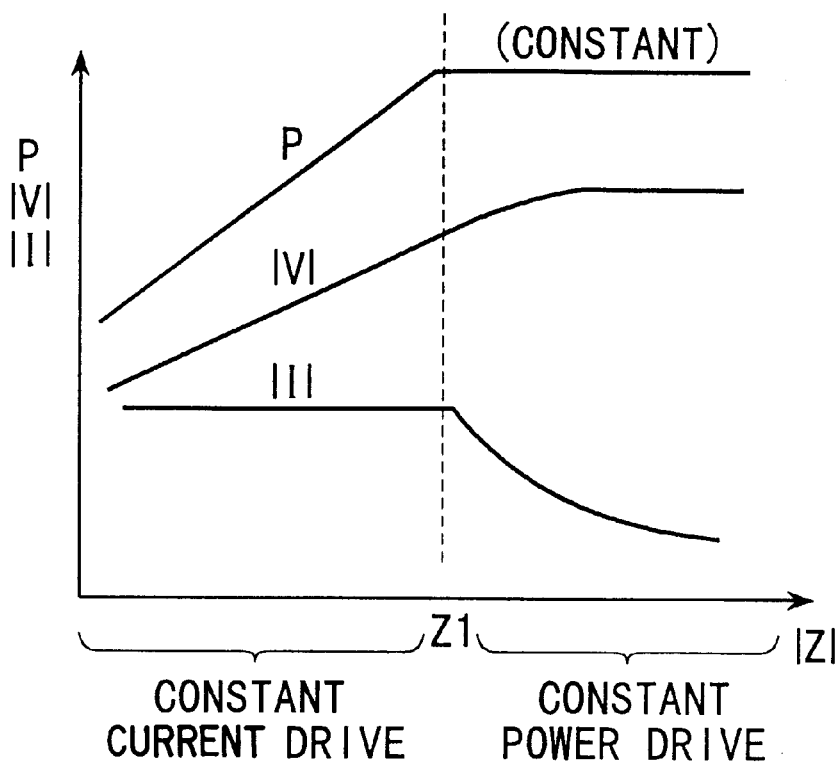
FIG. 10 is a characteristic graph showing characteristics of a main part of the ultrasonic operation apparatus according to the second embodiment, and specifically variations in current, voltage and power when the ultrasonic operation apparatus is used.

FIGS. 9 and 10 show a second embodiment of the invention. In this embodiment, the structure of the drive circuit 23 of ultrasonic operation apparatus 1 of the first embodiment (see FIGS. 1 to 7A and 7B) is replaced with the structure of drive circuit 51 shown in FIG. 9.

The drive circuit 51 of this embodiment, like the first embodiment, includes an output circuit wherein a phase-locked loop (PLL) 24, a voltage control amplifier (VCA) 25, a power amplifier 26, a voltage/current detector 27, and an output transformer 28 are connected in series. The drive circuit 51, like the first embodiment, also includes a differential amplifier 29 and a voltage generator 30.

The drive circuit 51 of this embodiment further includes signal generating means 52, a multiplier 53 and a differential amplifier 54. The signal generating means 52 sets a limit value of energy. The multiplier 53 multiplies a current value |I| and a voltage value |V| and produces a voltage corresponding to the magnitude of power |P|. The differential amplifier 54 compares an output signal from the signal generating means 52, as a reference signal, with an output signal from the multiplier 53, thereby controlling signal generation in the voltage generator 30 serving as current value setting means. Alternatively, the differential amplifier 54 may receive the energy limit set signal from the signal generating means 52, as a reference signal, and the magnitude of voltage as a comparative value. The output of the differential amplifier 54 controls the voltage generator 30 for generating a signal with a constant current set value. With the addition of the signal generating means 52, multiplier 53 and differential amplifier 54, the drive circuit 51 for constant power control is achieved.

The operation of the above structure will now be described. FIG. 10 illustrates a control method in this embodiment. In FIG. 10, the abscissa indicates a variation of impedance |Z|, and the ordinate indicates the magnitude of current |I|, the magnitude of voltage |V| and the magnitude of power |P|.

In the drive circuit 51 of this embodiment, the ultrasonic oscillator is resonance-point driven by the phase-locked loop (PLL) 24. Since the phase difference between the voltage and current is zero, the value obtained by multiplying the magnitude of voltage and the magnitude of current is exactly proportional to the power consumed by the ultrasonic transducer, and the power value can be easily measured.

In the ultrasonic operation apparatus 1 of this embodiment, e.g. ultrasonic coagulation/cutting apparatus, the amount of force, with which the treatment section 11 of handpiece 4 holds the living tissue H, influences the treatment result of the ultrasonic coagulation/cutting function. Similarly, in the case of another applied device, e.g. an ultrasonic clip, the amount of force for pushing the clip on the living tissue H influences the treatment result of respective functions. In the case of an ultrasonic trocar, the amount of force for piercing the trocar into the living tissue H influences the treatment result of each function. That is, such forces influence the exact coagulation treatment of living tissue H, exact clipping treatment or stable piercing treatment.

If the amount of such force increases, the mechanical load applied to the ultrasonic oscillator increases. Specifically, since electrical impedance $|Z|$ increases, the power $|P|$ supplied to the ultrasonic oscillator gradually increases. In the case of constant-current control, since the current value $|I|$ is controlled to be constant, the supply power $|P|$ increases as a result of the increase in voltage $|V|$, as shown in FIG. 10.

However, if the oscillation energy of the ultrasonic oscillator is not so great, the functions of coagulation treatment, clip treatment or piercing treatment are stabilized. In the present embodiment, the upper limit value for the energy amount is set so as to limit the upper limit of the output voltage from the drive circuit 51, i.e. the voltage applied to the ultrasonic oscillator. Specifically, as shown in FIG. 10, in a range of impedance $|Z|$ from a lower region to a preset value Z1, the constant-current drive control is performed. In this range, even if the impedance $|Z|$ increases, the current value $|I|$ is kept constant and the voltage $|V|$ increases in proportion to the increase in impedance $|Z|$. As a result, the power $|P|$ increases proportionally. If the range of variation of impedance $|Z|$ exceeds the set value Z1, the drive current value $|I|$ is decreased in a higher range of impedance $|Z|$ and similarly the rate of increase in voltage $|V|$ is decreased. Thus the upper limit value of power $|P|$ is controlled to be constant.

If the multiplier 53 in the drive circuit of this embodiment is omitted, a constant-voltage control drive circuit 51 is obtained. It is possible to constitute the drive circuit 51 of this embodiment by a D/A converter, an A/D converter and a CPU so that the drive circuit 51 functions similarly with the present embodiment. The control unit 2 may be provided with some display means or sound producing means for indicating switching from a constant current control to a constant voltage control or to a constant power control.

Figure 11:
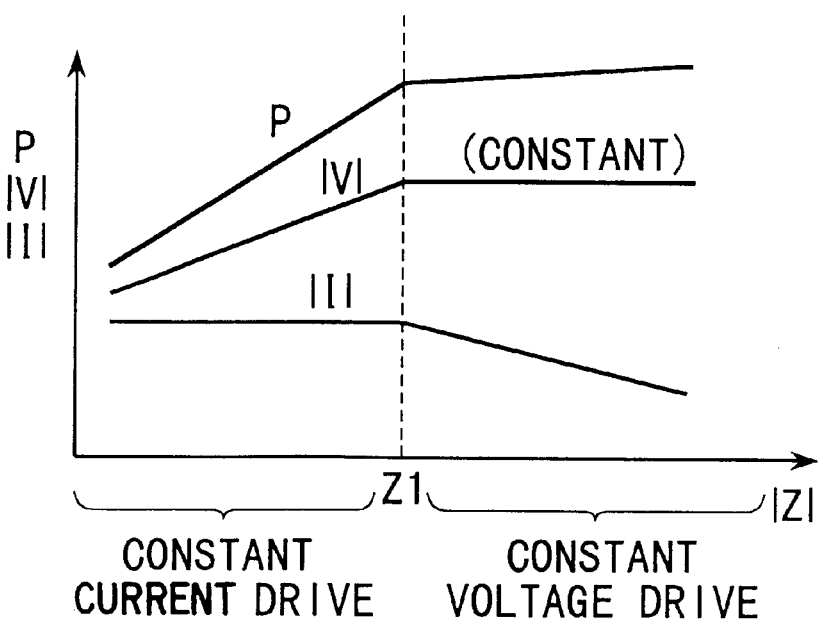
FIG. 11 is a characteristic graph showing characteristics of a main part of a modification of the ultrasonic operation apparatus according to the second embodiment.

FIG. 11 shows a modification of the second embodiment (see FIGS. 9 and 10). This modification can easily achieve the technique for keeping the power constant, as in the second embodiment.

In this modification, the constant current drive is performed similarly with the second embodiment until the impedance $|Z|$ reaches the preset value Z1. In a range over the preset value Z1, the magnitude of voltage value $|V|$ is set to be constant. In this case, the current value $|I|$ decreases and the value of power $|P|$ slightly increases. With this simple control, too, the upper limit can be set for the power $|P|$ as a result.

Figure 12A:
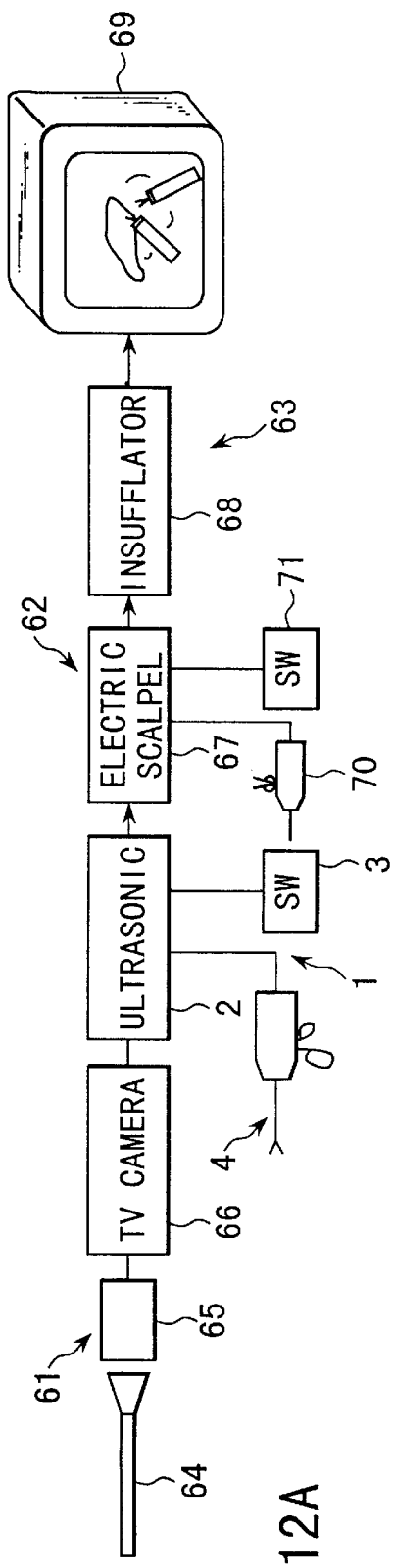
FIG. 12A shows a schematic structure of an entirety of an operation apparatus according to a third embodiment of the invention.
Figure 12B:
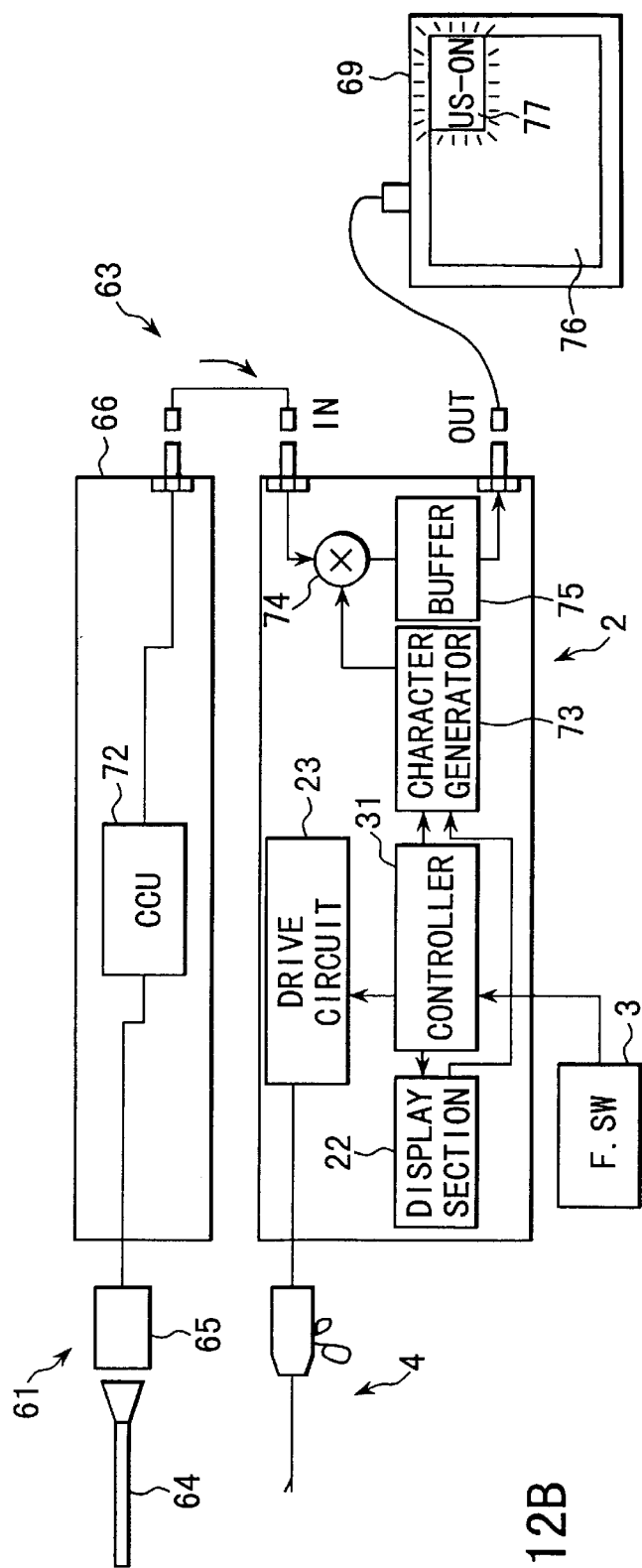
FIG. 12B shows a schematic structure of a drive circuit provided within a main body of the ultrasonic operation apparatus according to the third embodiment of the invention.

FIGS. 12A and 12B show a third embodiment of the invention. This embodiment relates to a method of indicating a control state, wherein the present invention is applied to an operation apparatus 63 comprising, as a combination, the ultrasonic operation apparatus 1 of the first embodiment (see FIGS. 1 to 7B), an endoscope system 61 and an electric scalpel apparatus 62.

FIG. 12A schematically shows the entire structure of the operation apparatus 63. Reference numeral 64 denotes a hard endoscope; 65 an endoscope camera head connected to the hard endoscope 64; 66 a TV camera processor connected to the camera head; 67 an electric scalpel device; 68 an insufflator; and 69 a monitor. The endoscope 64, camera head 65, TV camera processor 66, electric scalpel device 67, insufflator 68 and monitor 69 are serially connected. A handpiece 70 for the electric scalpel and a footswitch 71 for the electric scalpel are connected to the electric scalpel device 67.

A CCU 72 is mounted in the TV camera processor 66, as shown in FIG. 12B. An image obtained through the endoscope 64 is converted to an electric signal by the CCU 72.

The control unit 2 of the ultrasonic operation apparatus 1 includes a character generator 73 as well as the drive circuit for the ultrasonic treatment device, controller 31 and display section 22. The controller 31 and display section 22 are connected to the input side of the character generator 73.

The output side of the character generator 73 is connected to one input terminal of a superimposer 74. The other input terminal of the superimposer 74 receives an output signal from the CCU 72. An output terminal of the superimposer 74 is connected to an input terminal of a buffer 75. An output terminal of the buffer 75 is connected to a monitor 69. An indication information display region 77 is provided on a part of an image display screen 76 of the monitor 69. The indication information display region 77 displays information on the state of load on ultrasonic oscillation and other information.

The operation of the above structure will now be described. In this embodiment, information on desired items to be indicated, e.g. on/off state of ultrasonic output, is generated by the character generator 73 in the ultrasonic operation apparatus 1. The generated character signal is mixed with the output signal from the CCU 72 by the superimposer 74. The output signal from the superimposer 74 is amplified by the buffer 75 and then a TV signal is output as a monitor signal.

As is shown in FIG. 12B, for example, indication information on the on-state of the ultrasonic output is displayed in a superimposed manner on an upper right area of the monitor 69, that is, on the indication information display region 77 on a part of the image display screen 76 of monitor 69.

In a case where states of plural operation apparatuses are to be superimposed on a monitor image of the endoscopic image on the image display screen 76 of monitor 69, a special character generator for each operation apparatus has been required in the prior art. Accordingly, in the conventional apparatus, the character generator needs to be connected to the ultrasonic operation apparatus 1, electric scalpel device 67 or insufflator 68 and characters indicating the state thereof needs to be generated from the output signal therefrom. If a novel operation apparatus is developed in the conventional apparatus, the character generator needs to be modified.

By contrast, in the embodiment with the above structure, the superimposer 74 is built in the operation apparatus 63 for serial connection. Even if a new operation apparatus is added in this embodiment, the superimposer 74 can be serially connected to the new apparatus. Thus, superimposed information can be easily displayed on the indication information display region 77 on a part of the image display screen 76 of monitor 69.

Figure 13:
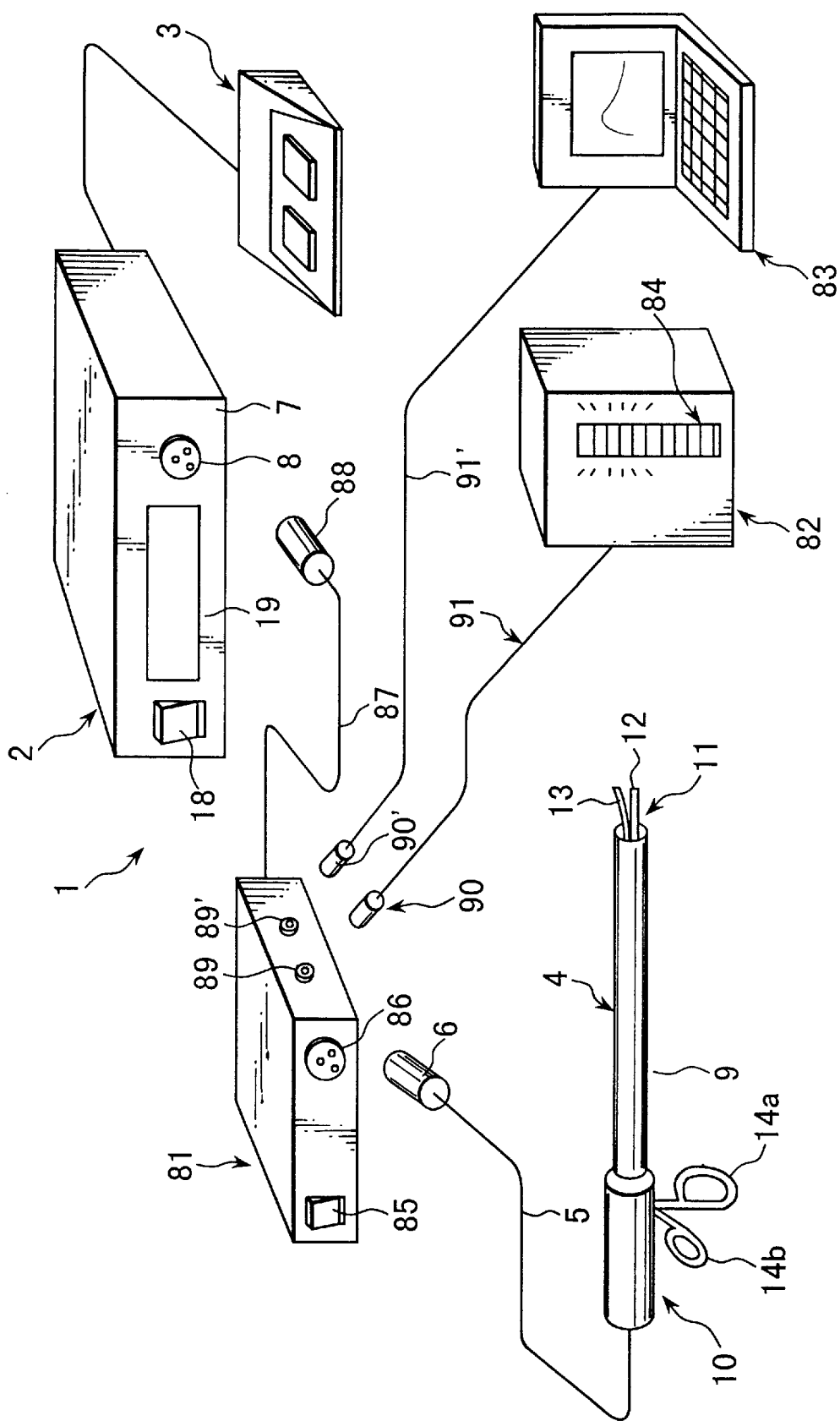
FIG. 13 shows a structure of an ultrasonic treatment apparatus according to a fourth embodiment of the invention.
Figure 14:
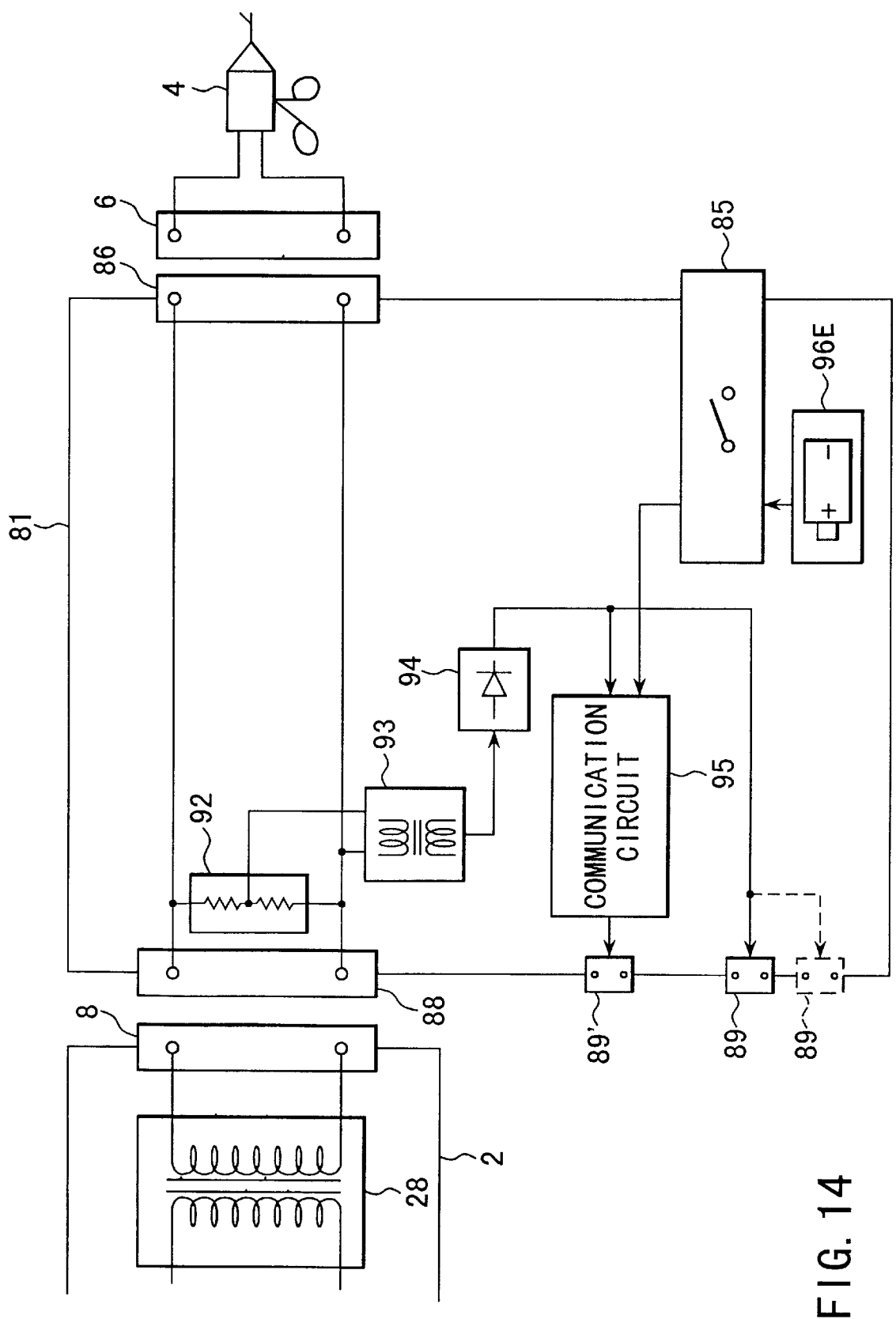
FIG. 14 shows a detailed structure of a drive state monitoring detector according to the fourth embodiment.

FIGS. 13, 14 and 16 show a fourth embodiment of the invention. FIG. 13 shows a structure of an ultrasonic treatment apparatus according to this embodiment. In the structure shown in FIG. 13, the ultrasonic operation apparatus of the first embodiment (see FIGS. 1 to 7B) is modified as follows. The bar-graph display section 22 is removed from the control unit 2 of the first embodiment. Moreover, a drive state monitor detector 81 and drive state monitor displays 82 and 83 are added. The drive state monitor detector 81 serves as signal detection means for electrically relaying the control unit 2 and handpiece 4 and detecting magnitudes of a voltage signal and a current signal supplied to the handpiece 4. The drive state monitor displays 82 and 83 serve as indication means which are detachably connected to the drive state monitor detector 81 and display detected signals as monitor results in different display modes.

The drive state monitor display 82 corresponds to the bar-graph display section 22 in the apparatus of the first embodiment. The drive state monitor display 82 includes a bar-graph display section 84 for effecting a bar-graph display by turning on/off lights in accordance with signals produced in the display circuit. The drive state monitor display 83 comprises a personal computer and displays a time-basis variation of detected data.

The drive state monitor detector 81 comprises, on its outer part, a power switch 85 for turning on/off a power supply in the detector 81, a drive state monitor connector which can be connected to the handpiece connector 6, a drive state monitor connector 88 which can be connected to the ultrasonic treatment device of control unit 2 via a relay cord 87, and output connectors 89 and 89' for outputting data detected by the drive state monitor detector 81. The drive state monitor display 82 can be connected to the output connector 89 via a display connector 90 and a relay cord 91. The drive state monitor display 83 can be connected to the output connector 89' via a display connector 90' and a relay cord 91'. The drive state monitor detector 81 and drive state monitor displays 82 and 83 constitute a drive state monitor unit.

According to this structure, a compact structure of the control unit 2 is achieved and the drive state monitor displays 82 and 83 can be arranged at desired positions. Thus, the displayed drive state can be easily recognized.

In the above structure, the bar-graph display 84 is provided only on the drive state monitor display 82. If easier recognition of displayed information is desired, another bar-graph display section may be provided on the control unit 2 and/or drive state monitor detector 81. In a case where the drive state monitor detector 81 is placed near the control unit 2, for example, on the control unit 2, the length of the relay cord 87 may be decreased. If the drive state monitor detector 81 is situated at a position away from the control unit 2, a relatively long relay cord 87 is used.

FIG. 14 shows a detailed structure of the drive state monitor detector 81 according to the fourth embodiment of the invention. The drive state monitor detector 81 comprises a voltage dividing circuit 92, an insulation transformer 93 and a rectifying/smoothing circuit 94. The voltage dividing circuit 92 divides a voltage of an ultrasonic signal supplied from the control unit 2 to the handpiece 4. The insulation transformer 93 insulates a voltage signal from the voltage dividing circuit 92. The rectifying/smoothing circuit 94 rectifies and smoothes a voltage signal detected by the insulation transformer 93 and produces a DC voltage. The DC voltage from the rectifying/smoothing circuit 94 is supplied as a detection result to the drive state monitor display 82 via the output connector 89 by analog data transfer, and the detection result is displayed in the form of a bar graph. At the same time, the DC voltage from the rectifying/smoothing circuit 94 is processed by a communication circuit 95 serving as conversion means for performing serial communication, and then it is supplied to the drive state monitor display 83 via the output connector 89'. Thus, time-basis variation of data is displayed.

Reference numeral 96E denotes a power supply circuit serving as means for supplying power to the communication circuit 95 upon the operation of the power switch 85. A commercial power supply or a battery is used as the power supply circuit 96. The use of the battery is advantageous in that insulation means for protecting a patient is not needed and the drive state monitor detector 81 can be situated at a desired position away from the location of the commercial power supply.

Figure 24:
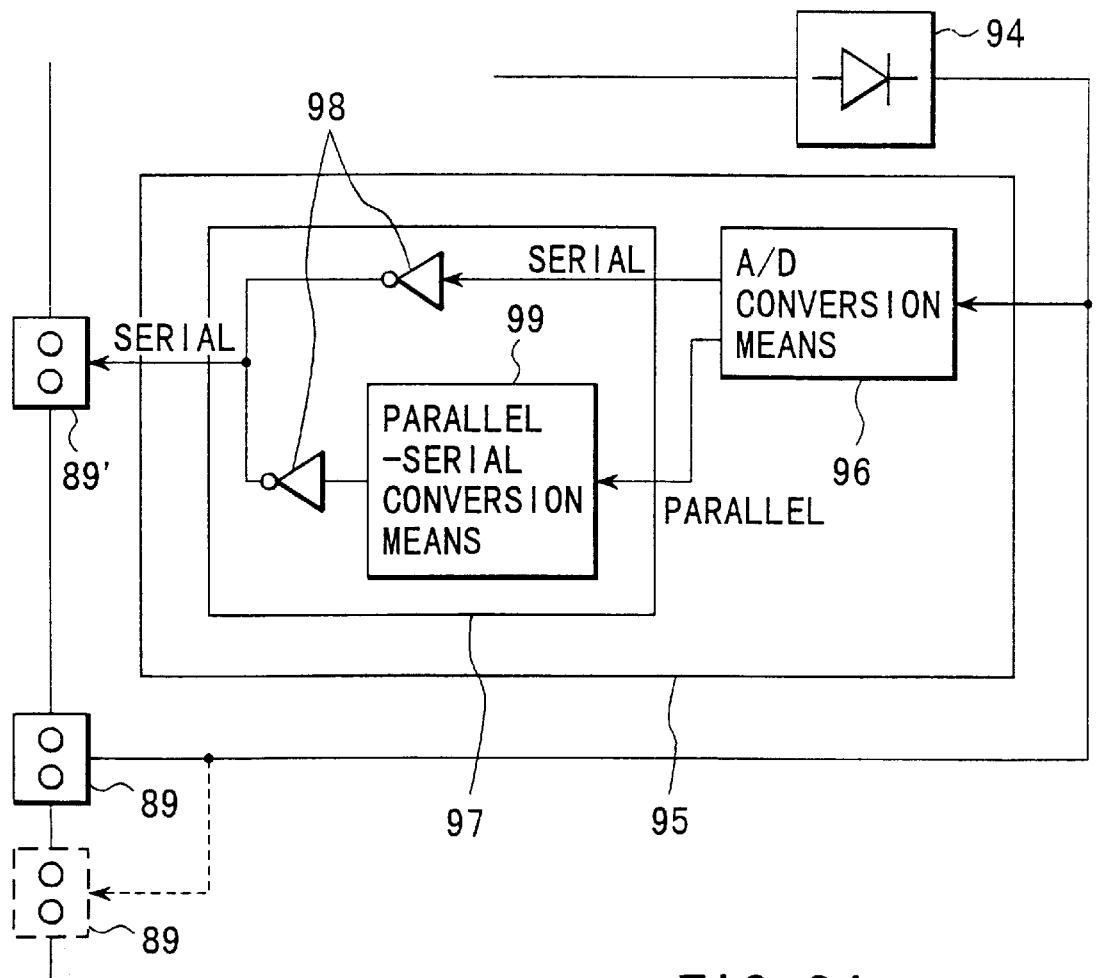
FIG. 24 shows an internal structure of a communication circuit of the drive state monitoring detector according to the fourth embodiment.

FIG. 24 shows a structure of the communication circuit 95 shown in FIG. 14. The communication circuit 95 comprises A/D (analog/digital) conversion means 96 and communication means 97. The communication means 97 includes communication buffer means 98 and parallel/serial conversion means 99.

When the communication circuit 95 is operated, a DC voltage input from the rectifying/smoothing circuit 94 to the communication circuit 95 is converted to a digital signal through the A/D conversion means 96 and is output to the outside from the output connector 89' by means of the communication means 97. When a digital conversion result obtained by the A/D conversion means 96 is serial data, the communication means 97 becomes communication buffer means 98. If the digital conversion result in the A/D conversion means 96 is parallel data, the communication means 97 becomes communication means having the parallel/serial conversion means 99.

Needless to say, the above-described advantages can be obtained even if the conversion result of the A/D conversion means 96 of communication circuit 95 is parallel data, the communication means 97 is constituted by the communication buffer means 98 and the communication circuit 95 becomes the conversion means for performing parallel communication.

In addition, even if the power switch 85 is operated to shut off the power supply circuit 96E and the communication circuit 95 does not operate, the ultrasonic signal supplied from the control unit 2 to the handpiece 4 is relayed and the ultrasonic signal is not influenced by the turning on/off of the power switch 85.

Figure 15:
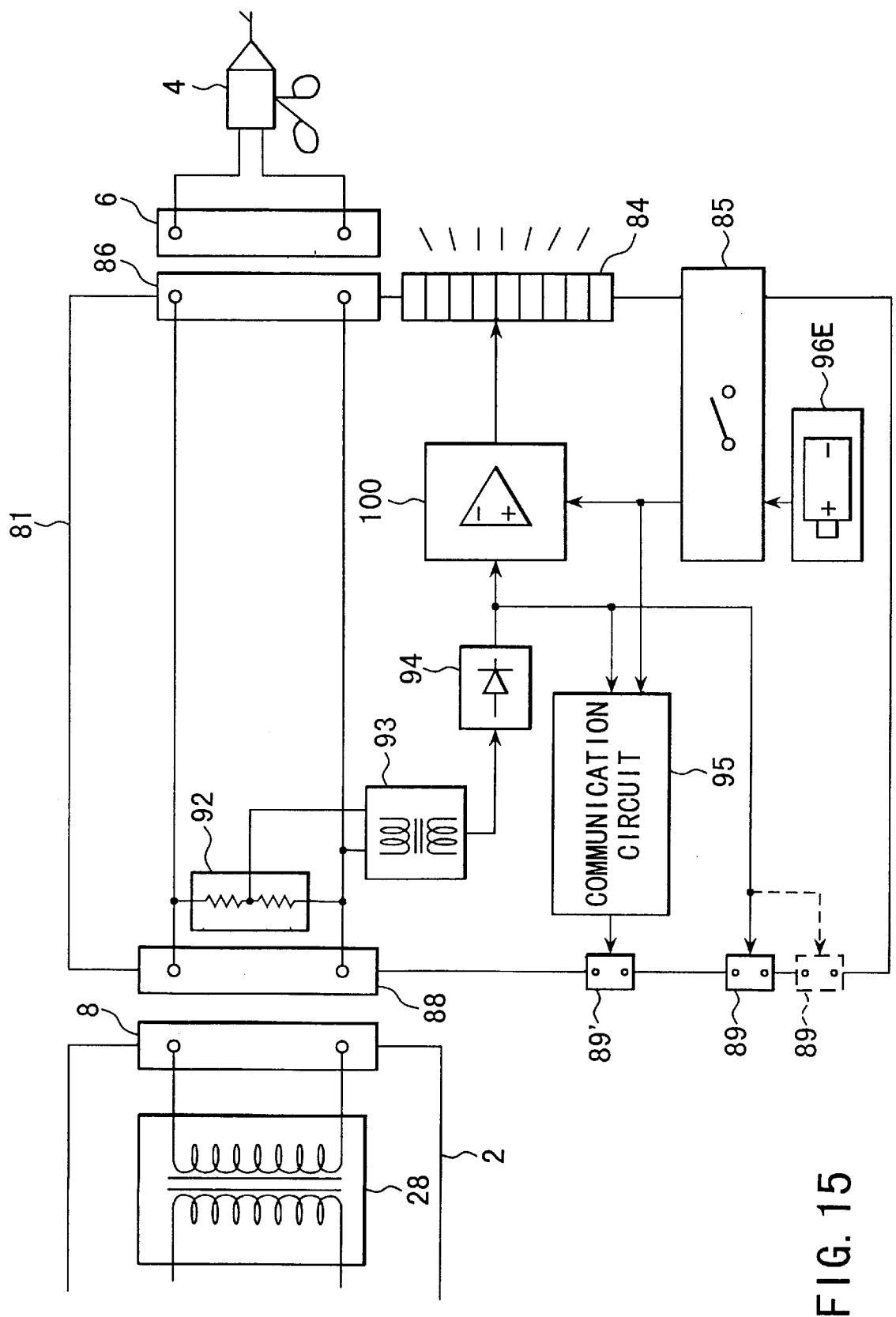
FIG. 15 shows a structure of a modification of the fourth embodiment, wherein the drive state monitoring detector and a drive state monitor display are integrated.

FIG. 15 shows a modification of the structure shown in FIG. 14, wherein the drive state monitor detector 81 and drive state monitor display 82 are integrated. In addition to the structure shown in FIG. 14, the structure in FIG. 15 includes a display circuit 100 for determining turning on/off the bar-graph display section 84 from the DC voltage of the rectifying/smoothing circuit 94, and the bar-graph display section 84 which is turned on/off in accordance with the signal from the display circuit 100. Power is supplied to the display circuit 100 from the power supply circuit 96E.

FIG. 16 shows detailed structures of the display circuit 100 and bar-graph display section 84. The display circuit 100 comprises a resistor group 101 and a comparator group 102. The resistor group 101 determines a reference voltage (resolution) to input terminals of the comparator group 102.

One input terminal of each comparator 102 receives the reference voltage from the resistor group 101, and the other input terminal of each comparator 102 receives detection data from the rectifying/smoothing circuit 94, thereby determining turning-on/off of LEDs of the LED group 103 of the next-stage bar-graph display section 84. Specifically, LEDs selected among the LED group 103 are turned on in accordance with the magnitude of detection data, and thus the drive state of the ultrasonic oscillator is displayed in the form of a bar graph.

FIG. 17 shows a modification of the display circuit 100 shown in FIG. 16. The display circuit 100 includes, in addition to the comparator group 102, resistor groups 101a, 101b and 101c, a change-over switch 104 for selecting one of the resistor groups 101a, 101b and 101c, and a selector circuit 105 for determining which of the resistor groups is to be selected by the change-over switch 104 by the turning of a dial 105a. Although FIG. 17 shows only three resistor groups 101a, 101b and 101c, the number of resistor groups may be freely chosen.

According to the structure shown in FIG. 17, one of the resistor groups is properly selected by the selector circuit 105 in combination with the setting by the setting section 21. Thereby, the dynamic range of the bar-graph display can be increased while maintaining a desired resolution.

Figure 18:
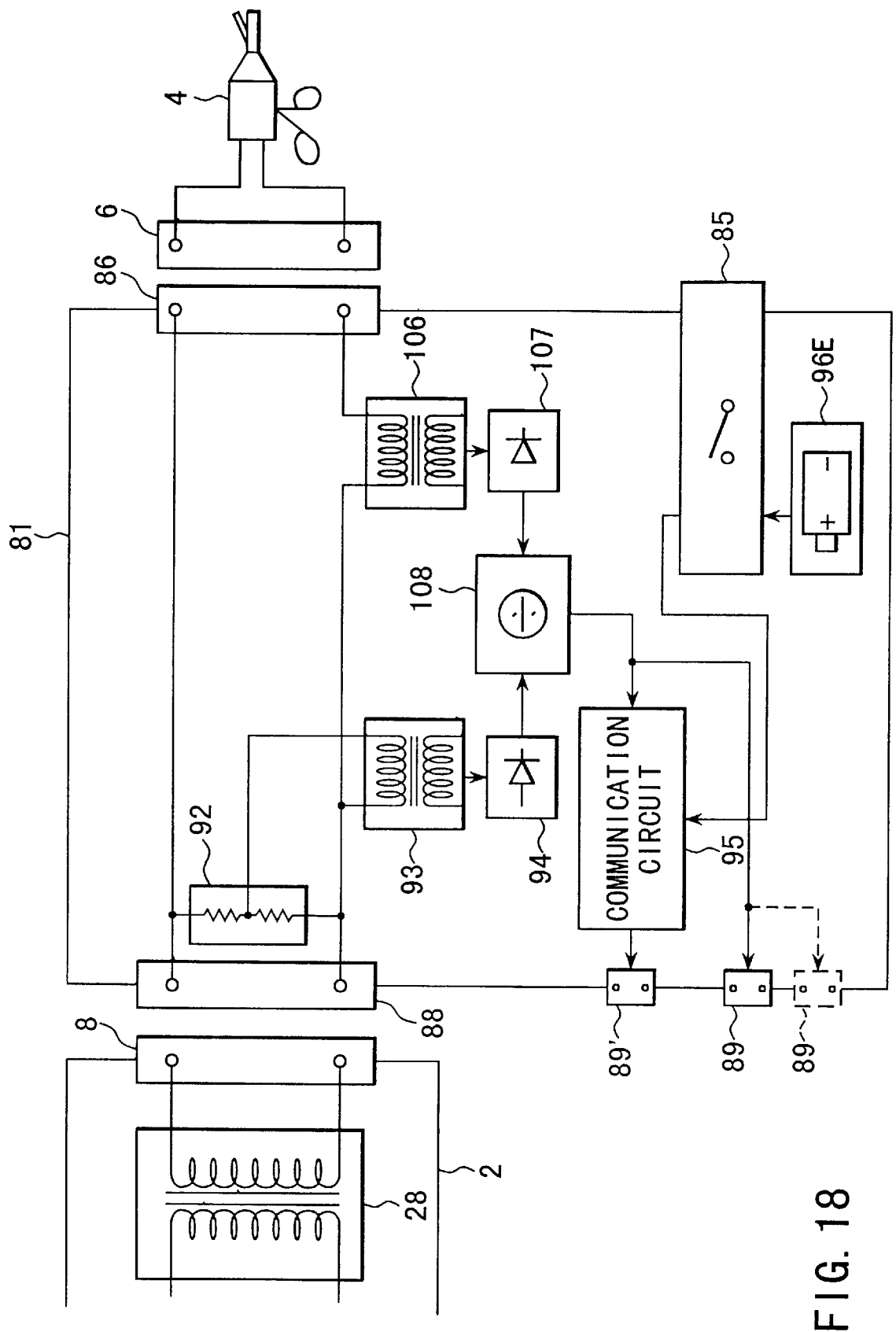
FIG. 18 shows a structure of a drive state monitoring detector according to a fifth embodiment of the invention.

FIG. 18 shows a structure of a drive state monitor detector 81 according to a fifth embodiment of the invention. In the fifth embodiment, in addition to the structure shown in FIG. 14, the following are provided: an insulation transformer 106 for insulating and detecting electric current energy supplied to the handpiece 4, a rectifying/smoothing circuit 107 for rectifying and smoothing the electric current signal detected by the insulation transformer 106 to obtain a DC signal, and a division circuit 108 for receiving the rectified/smoothed current signal and a voltage signal from the rectifying/smoothing circuit 94 and dividing the voltage signal by the current signal.

A division result by the division circuit 108 is supplied as a detection result to the drive state monitor display 82 via the output connector 89 by analog data transfer and is displayed in the form of a bar graph. At the same time, the division result is processed by the communication circuit 95 serving as conversion means for performing serial communication and then supplied to the drive state monitor display 83 via the output connector 89', and a time-basis variation of data is displayed.

According to the present embodiment, as described above, the current supplied to the handpiece 4 is detected in addition to the detection of voltage, and the detected voltage signal is divided by the current signal. In a case where a large current value is set, even if the voltage signal increases consequently from the formula, V (voltage)=I|Z| (current X electric impedance), the value obtained by division of V/I is substantially equal and a substantially constant dynamic range is obtained. Accordingly, the bar graph display can be effected even if the user does not adjust the current value set by the setting section 21. Moreover, since the dynamic range becomes substantially constant, the number of resistor groups in the display circuit may be one when the division result is displayed and the structure of the embodiment can be reduced in size.

Figure 19:
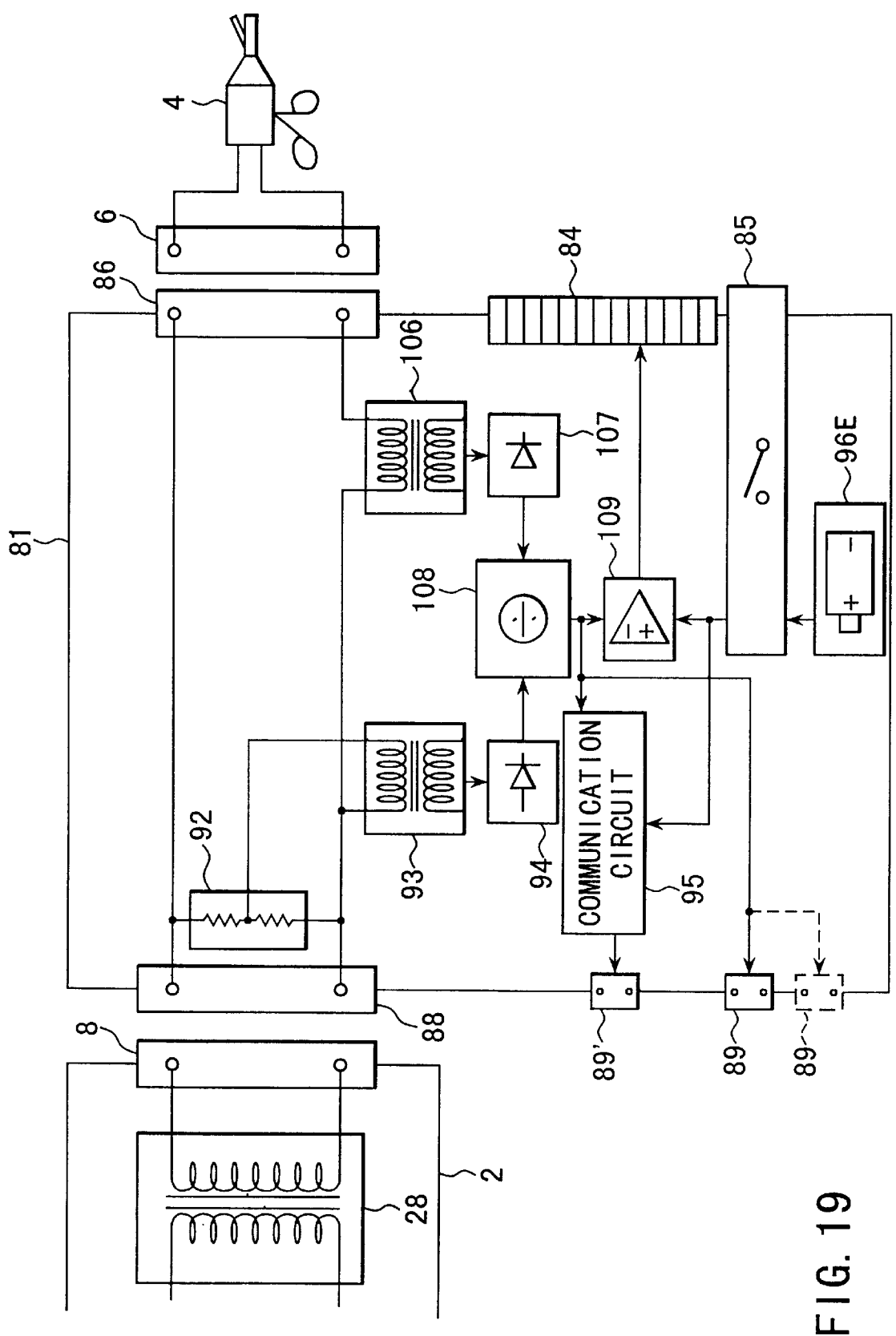
FIG. 19 shows a structure of a modification of the fifth embodiment, wherein the drive state monitoring detector and a drive state monitor display are integrated.

FIG. 19 shows a modification of the structure shown in FIG. 18, wherein the drive state monitor detector 81 and drive state monitor display 82 are integrated. In addition to the structure shown in FIG. 18, the structure in FIG. 19 includes a display circuit 109 for determining turning on/off the bar-graph display section 84 from the division result of the division circuit 108, and the bar-graph display section 84 which is turned on/off in accordance with the signal from the display circuit 109. Power is supplied to the display circuit 109 from the power supply circuit 96E.

Figure 20:
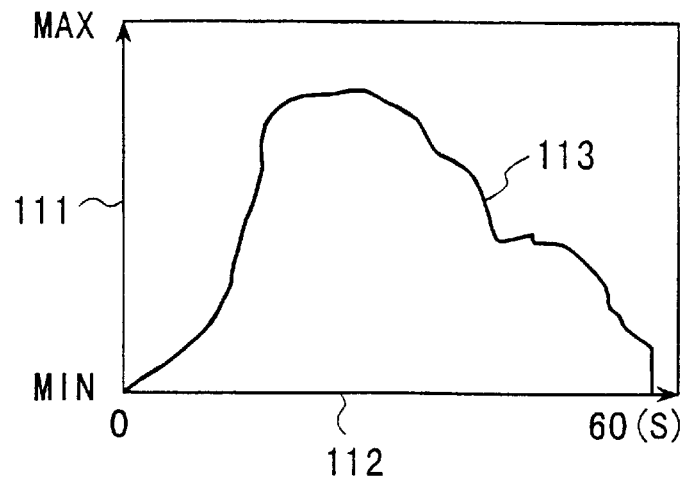
FIG. 20 shows an example of a display image on the drive state monitor display.

FIG. 20 shows an example of display content of the drive state monitor display 83 comprising a personal computer, etc. In FIG. 20, an ordinate 111 indicates electric impedance |z| (proportional to the magnitude of drive state), and an abscissa 112 indicates passing of time. Numeral 113 indicates a time-basis monitor result of the drive state.

Figure 21:
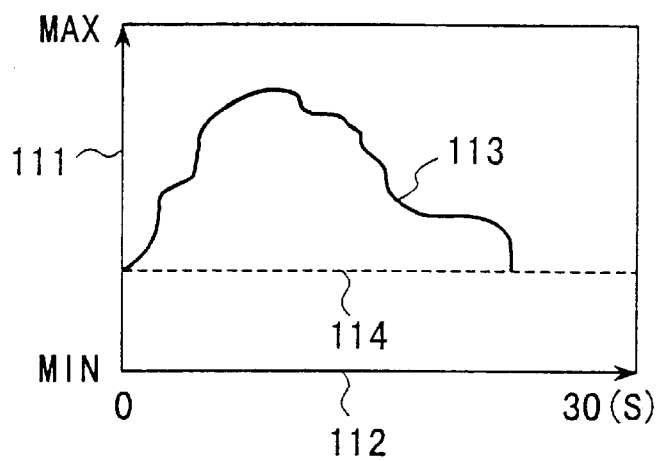
FIG. 21 shows another example of a display image on the drive state monitor display.

FIG. 21 shows another example of display content of the drive state monitor display 83. In this example, display begins only after the drive state exceeds a threshold. Numeral 114 indicates a threshold line for this purpose. With the addition of the threshold line 114, the drive state can be better understood. In FIGS. 20 and 21, the setting of the time width on the time axis can be varied. In addition, the position on the screen of the threshold line 114 in FIG. 21 can also be varied.

In the above embodiment, the number of output connectors 89 for analog-transferring detected data has been described as being one. However, as indicated by broken lines in FIGS. 14, 15, 18 and 19, another or two or more similar connectors may be added and drive state monitor displays 82 may be provided for the respective output connectors 89. Thereby, the visual recognition of bar-graph display can be further enhanced.

Figure 22:
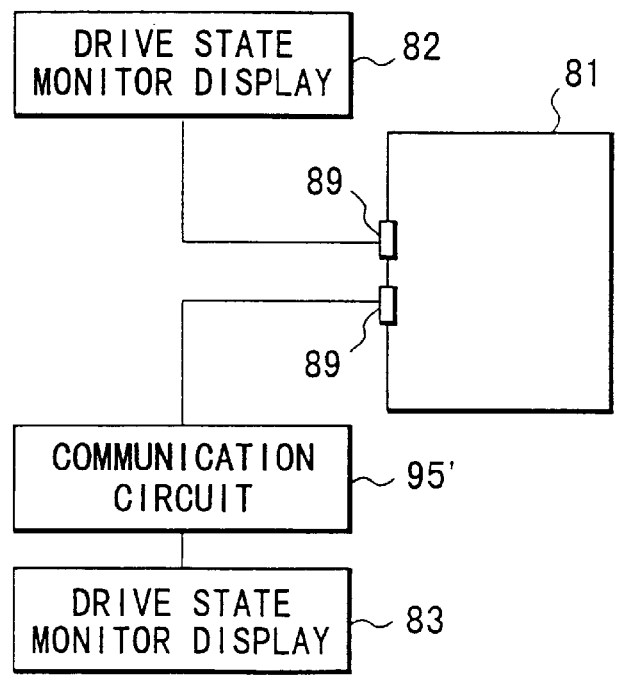
FIG. 22 shows another example of the structure of the ultrasonic treatment apparatus.

As is shown in FIG. 22, one of the two output connectors 89 of the drive state monitor detector 81 may be connected to the drive state monitor display 82, the other output connector 89 may be connected to a communication circuit 95' having a communication process function and an A/D conversion function similar to those of the communication circuit 95, and the communication circuit 95' may be connected to the drive state monitor display 83 such as a personal computer. In this case, the communication circuit 95 and output connector 89' provided in the drive state monitor detector 81 may be dispensed with. With this structure, the personal computer need not have the A/D conversion function.

Figure 23:
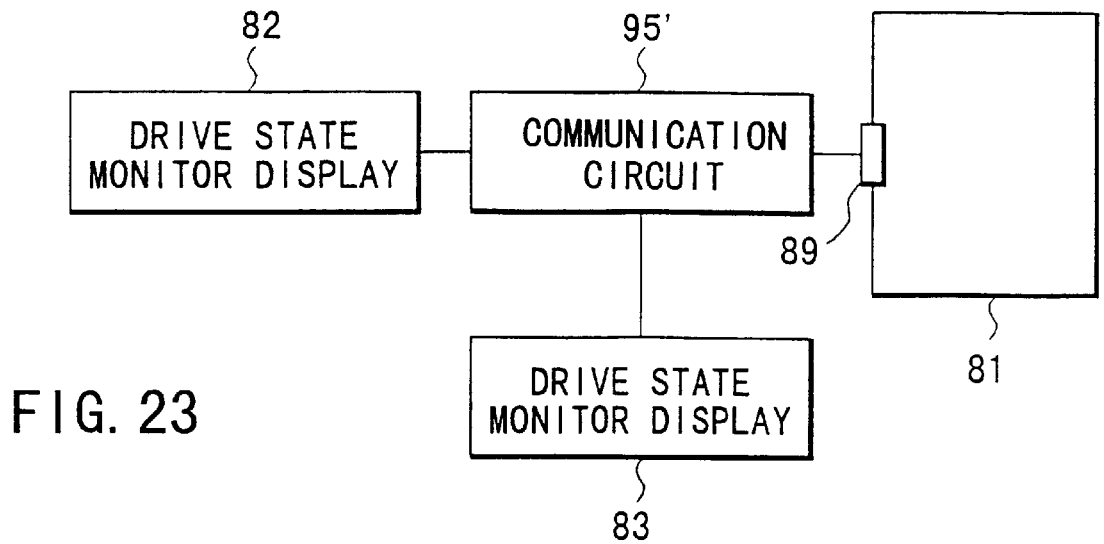
FIG. 23 shows still another example of the structure of the ultrasonic treatment apparatus.

As is shown in FIG. 23, one output connector 89 for analog transfer may be provided, the above-mentioned communication circuit 95' may be connected to this output connector 89, and the drive state monitor displays 82 and 83 may be connected to the communication circuit 95'.

In the above embodiments, the ultrasonic coagulation/cutting apparatus was described by way of example. This invention, however, is applicable to another type of ultrasonic treatment apparatus, e.g. an ultrasonic suction apparatus.

In the above embodiments, the drive state of the ultrasonic oscillator is visually displayed by the drive state monitor displays 82 and 83. However, the detected voltage signal may be converted to a frequency through frequency conversion means, and the detected voltage signal may be indicated as a variation in sound quality by sound producing means in accordance with a variation of the signal from the frequency conversion means.

Figure 25:
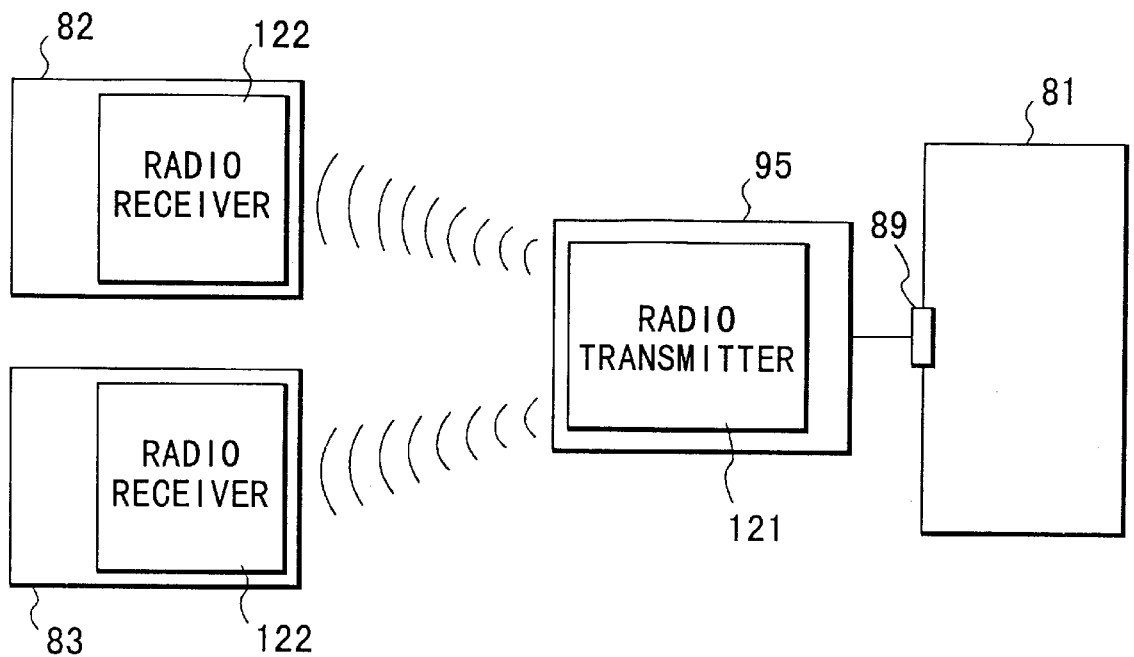
FIG. 25 shows a modification of a communication circuit on a drive state monitor detector side and a communication means on a drive state monitor display side.

Besides, as shown in FIG. 25, the communication circuit 95 connected to the output connector 89 of drive state monitor detector 81 may be provided with a radio transmitter 121, and radio receivers 122 may be provided in the drive state monitor displays 82 and 83. In this case, the detected voltage signal is converted to a radio communication signal by conversion means, and the communication signal is radio-transmitted between the radio transmitter 121 of the communication circuit 95 and the radio receivers 122 of the drive state monitor displays 82 and 83.

Figure 26:
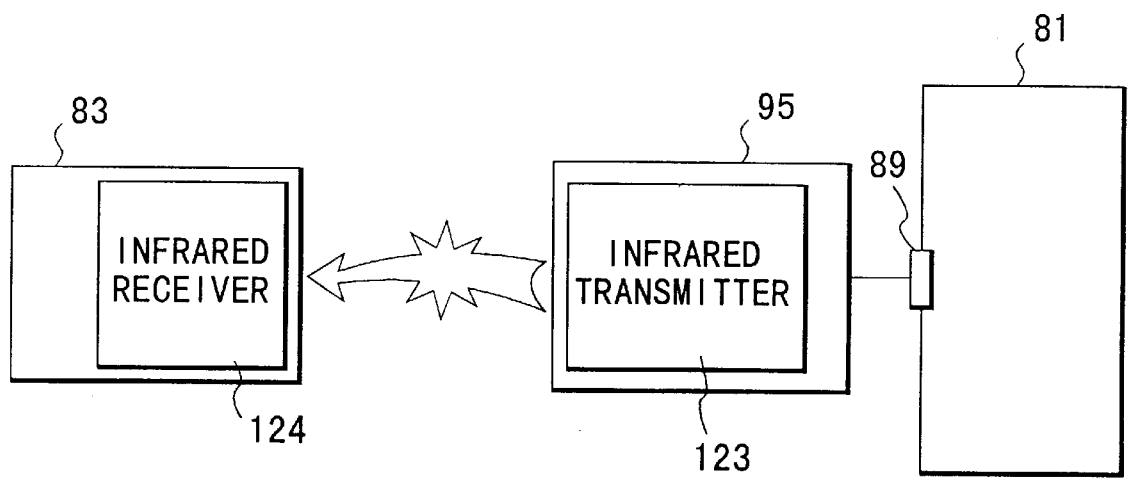
FIG. 26 shows another modification of a communication circuit on a drive state monitor detector side and a communication means on a drive state monitor display side.

Furthermore, as shown in FIG. 26, the communication circuit 95 connected to the output connector 89 of drive state monitor detector 81 may be provided with an infrared transmitter 123, and infrared receivers 124 may be provided in the drive state monitor displays 82 and 83. In this case, the detected voltage signal is converted to an infrared communication signal by conversion means, and the communication signal is infrared-transmitted between the infrared transmitter 123 of the communication circuit 95 and the infrared receivers 124 of the drive state monitor displays 82 and 83. The radio or infrared communication means may be replaced with optical communication means (not shown). Needless to say, the same advantages can be obtained in this case.

Of course, the present invention is not limited to the above embodiments, and various modifications may be made without departing from the spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. An ultrasonic operation apparatus comprising a drive circuit unit connected to a handpiece, wherein:
   (i) said handpiece comprises:
      an ultrasonic oscillator;
      a treatment section for holding a living tissue;
      a probe for transmitting ultrasonic oscillation from the ultrasonic oscillator to the treatment section; and
      a hold operation section for operating the treatment section; and
   (ii) said drive circuit unit comprises:
      a drive circuit for driving the ultrasonic oscillator;
      load state detection means for detecting a load state of a load acting on the treatment section when the treatment section holds the living tissue; and
      load state indicating means for indicating the load state in relation to the ultrasonic oscillation based on a detection result from the load state detection means.

2. The apparatus according to claim 1, wherein:
   said drive circuit comprises constant current control means for performing a control operation to enable a predetermined constant current flow to the ultrasonic oscillatory; and
   said load state detection means includes means for taking out a signal indicating a magnitude of a voltage applied to the ultrasonic oscillator and determining the load state of the load acting on the treatment section based on a variation in the taken-out signal.

3. The apparatus according to claim 2, wherein:
   (i) said means for determining the load state comprises:
      voltage detection means for detecting a magnitude of a voltage signal supplied to the ultrasonic oscillator;
      reference voltage setting means for setting a predetermined reference voltage; and
      determination means having a plurality of comparators for comparing the reference voltage set by the reference voltage setting means and the detected magnitude of the voltage signal, and for determining a ratio of the detected magnitude of the voltage signal to the reference voltage; and
   (ii) said load state indicating means comprises a bar graph in which a plurality of light emitting diodes are juxtaposed, and selectively controls light emission states of the light emitting diodes based on a determination result of the determination means, and displays a level of the load state.

4. The apparatus according to claim 2, wherein:
   said means for determining the load state includes a voltage-frequency converter for converting a variation in the magnitude of the voltage signal applied to the ultrasonic oscillator to a variation in frequency; and
   the load state indicating means includes sound producing means for producing a sound with a sound quality varying in accordance with the magnitude of the voltage signal applied to the ultrasonic oscillator.

5. The apparatus according to claim 1, wherein said load state indicating means includes a display for displaying the load state of the treatment section based on a magnitude of a voltage applied to the ultrasonic oscillator.

6. The apparatus according to claim 1, wherein said drive circuit unit comprises the load state indicating means as a separate body.

7. The apparatus according to claim 1, wherein:
   said load state detection means includes a detachable connection portion permitting an electrical relay between the handpiece and the drive circuit unit, and signal detection means for detecting a signal supplied to the ultrasonic oscillator; and
   said load state indicating means includes a drive state monitor unit for indicating, as a monitor result, the signal detected by the signal detection means.

8. The apparatus according to claim 7, wherein:
   (i) said signal detection means comprises:
      voltage detection means for detecting a magnitude of a voltage signal supplied to the ultrasonic oscillator;
      reference setting means for setting a predetermined reference voltage; and
      determination means having a plurality of comparators for comparing the reference voltage set by the reference voltage setting means and the detected magnitude of the voltage signal, and for determining a ratio of the detected magnitude of the voltage signal to the reference voltage; and
   (ii) said load state indicating means comprises light emitting means for performing a level display by means of a plurality of light emitting diodes based on a result determined by the determination means.

9. The apparatus according to claim 8, wherein said light emitting means level-displays the ratio determined by the determination means to a maximum value by means of the plurality of light emitting diodes.

10. The apparatus according to claim 8, wherein said reference voltage setting means comprises:
    a plurality of reference voltage setting elements; and
    a switch for switching the reference voltage setting elements.

11. The apparatus according to claim 7, wherein:
    (i) said signal detection means comprises:
       voltage detection means for detecting a magnitude of a voltage signal supplied to the ultrasonic oscillator; and
       A/D conversion means for analog/digital converting the detected magnitude of the voltage signal, and ii) the load state indicating means comprises:
   a microprocessor for processing in real time digital data obtained by the A/D conversion means; and
   a display for displaying data processed by the microprocessor in accordance with time on at least one of a LCD screen and a CRT screen.

12. The apparatus according to claim 7, wherein:
(i) said signal detection means comprises:
   voltage detection means for detecting a magnitude of a voltage signal supplied to the ultrasonic oscillator; and
   frequency conversion means for voltage/frequency converting the detected magnitude of the voltage signal, and
(ii) said load state indicating means comprises sound producing means for outputting a variation of an output from the frequency conversion means as a variation of sound quality.

13. The apparatus according to claim 7, wherein said signal detection means comprises:
   voltage detection means for detecting a magnitude of a voltage signal supplied to the ultrasonic oscillator;
   conversion means for converting the detected magnitude of the voltage signal to a communication signal; and
   communication means for wirelessly communicating data converted by the conversion means.

14. The apparatus according to claim 7, wherein said communication means comprises one of an electric wave, infrared radiation, and an optical signal.

15. The apparatus according to claim 7, wherein:
(i) said signal detection means comprises:
   current detection means for detecting a signal indicating a magnitude of a current applied to the ultrasonic oscillator;
   voltage detection means for detecting a signal indicating a magnitude of a voltage applied to the ultrasonic oscillator; and
   arithmetic means for performing a predetermined arithmetic operation based on the signals detected by the current detection means and the voltage detection means; and
(ii) the load state indicating means comprises a display for displaying an arithmetic operation result obtained by the arithmetic means as a monitor result of the drive state.

16. The apparatus according to claim 7, wherein said load state indicating means comprises:
   a first drive state monitor display for displaying the detected load state as a monitor result in the form of a bar graph; and
   a second drive state monitor display for displaying a time-basis variation of the detected load state as a monitor result.

17. The apparatus according to claim 16, wherein:
said signal detection means comprises a first connection portion and a second connection portion for analog data transfers;
the first drive state monitor display is connected to the first connection portion; and
the second drive state monitor display is connected to the second connection portion via a communication circuit with an A/D conversion function.

18. The apparatus according to claim 16, wherein:
said signal detection means comprises an analog connection portion for analog data transfer;
the analog connection portion has an A/D conversion function and is connected to a communication circuit having a first connection portion for analog data transfer and a second connection portion for digital data transfers;
the first drive state monitor display is connected to the first connection portions; and
the second drive state monitor display is connected to the second connection portion.

19. The apparatus according to claim 7, wherein said signal detection means includes insulation means for insulating a signal supplied to the ultrasonic oscillator, and means for effecting signal detection.

20. The apparatus according to claim 7, wherein at least one of the signal detection means and the load state indicating means comprises a power supply.

21. The apparatus according to claim 20, wherein said power supply comprises a secondary power supply which is insulated from at least a commercial power supply.

22. An ultrasonic operation apparatus comprising:
   a handpiece with a treatment section for treating a living tissue;
   an ultrasonic oscillator built in the handpiece;
   a probe for transmitting ultrasonic oscillation from the ultrasonic oscillator to the treatment section; and
   a drive circuit unit connected to the handpiece and including a drive circuit for driving the ultrasonic oscillator;
   wherein said drive circuit unit comprises load state detection means for detecting a load state of a load acting on the treatment section when the treatment section is put in contact with the living tissue, said load state detection means comprising:
      a detachable connection portion permitting an electrical relay between the handpiece and the drive circuit unite; and
      signal detection means for detecting a signal supplied to the ultrasonic oscillator, said signal detection means being detachably connected to an external display and including an output section for outputting a control signal for displaying the load state relative to the ultrasonic oscillation on the external display and indicating the load state based on a detection result of the signal detection means when the external display is connected to said signal detection means.

23. An ultrasonic operation apparatus comprising a drive circuit unit connected to a handpiece, wherein:
(i) said handpiece comprises:
   an ultrasonic oscillator
   a treatment section for holding a living tissue;
   a probe for transmitting ultrasonic oscillation from the ultrasonic oscillator to the treatment section; and
   a hold operation section for operating the treatment section; and
(ii) said drive circuit unit comprises:
   a drive circuit for driving the ultrasonic oscillator;
   constant current control means for controlling a constant current control system to supply a predetermined constant current flow to the ultrasonic oscillator;
   means for taking out a signal indicating a magnitude of a voltage applied to the ultrasonic oscillator;
   means for setting a limit to the amount of energy supplied to the ultrasonic oscillator; and
   energy limit control means for switching, when the amount of energy supplied to the ultrasonic oscillator has reached the set limit, from the constant current control system controlled by the constant current control means to an energy amount limit control drive system for limiting the amount of energy supplied to the ultrasonic oscillator, in order to thereby drive the ultrasonic oscillator.

24. The apparatus according to claim 23, wherein said energy limit control means comprises:

signal generating means for generating a signal indicating a power supplied to the ultrasonic oscillator based on a variation in values of current and voltage supplied to the ultrasonic oscillator; and drive means for effecting an energy limit control operation for maintaining the signal from the signal generating means at said set limit.

25. The apparatus according to claim 23, wherein said energy limit control means comprises:

maximum voltage limit means for limiting a maximum voltage supplied to the ultrasonic oscillator based on a variation in a voltage supplied to the ultrasonic oscillator; and constant voltage drive means for maintaining the voltage supplied to the ultrasonic oscillator at a constant value.

26. An ultrasonic operation apparatus comprising:

a handpiece with a treatment section for treating a living tissue;

an ultrasonic oscillator built in the handpiece;

a probe for transmitting ultrasonic oscillation from the ultrasonic oscillator to the treatment section;

a hold operation section for operating the treatment section;

a connector section which can be detachably connected with said handpiece; and a drive circuit unit including a drive circuit for driving the ultrasonic oscillator by an ultrasonic drive signal generated in the drive circuit via the connector section;

wherein said drive circuit unit comprises:

load state detection means for detecting a load state of a load acting on the treatment section when the treatment section holds the living tissue; and load state indicating means for indicating the load state in relation to the ultrasonic oscillation based on a detection result from the load state detection means.

27. An ultrasonic operation apparatus comprising:

a handpiece with a treatment section for treating a living tissue;

an ultrasonic oscillator built in the handpiece;

a probe for transmitting ultrasonic oscillation from the ultrasonic oscillator to the treatment section;

a hold operation section for operating the treatment section; and a drive circuit unit connected to the handpiece and including a drive circuit for driving the ultrasonic oscillator;

wherein said drive circuit unit comprises load state detection means for detecting a load state of a load acting on the treatment section when the treatment section holds the living tissue, said load state detection means comprising:

a detachable connection portion permitting a relay between the handpiece and the drive circuit unit; and signal detection means for detecting a signal supplied to the ultrasonic oscillator, said signal detection means being detachably connected to an external display and including an output section for outputting a control signal for displaying the load state relative to the ultrasonic oscillator on the external display and indicating the load state based on a detection result of the signal detection means when the external display is connected to said signal detection means.

* * * * *